United States Patent
Banas et al.

(10) Patent No.: US 11,871,749 B2
(45) Date of Patent: *Jan. 16, 2024

(54) ALCOHOL-FREE HYDROGEN PEROXIDE DISINFECTANT COMPOSITIONS AND METHODS OF USE THEREOF

(71) Applicant: ALDEN MEDICAL, LLC, West Springfield, MA (US)

(72) Inventors: Carl F. Banas, West Springfield, MA (US); Christopher C. Valdes, West Springfield, MA (US); David Rinaldi, West Springfield, MA (US); Christopher A. Corridan, West Springfield, MA (US); Damon J. D'Amico, West Springfield, MA (US)

(73) Assignee: ALDEN MEDICAL, LLC, West Springfield, MA (US)

( * ) Notice: Subject to any disclaimer, the term of this patent is extended or adjusted under 35 U.S.C. 154(b) by 7 days.

This patent is subject to a terminal disclaimer.

(21) Appl. No.: 17/856,665

(22) Filed: Jul. 1, 2022

(65) Prior Publication Data

US 2022/0330552 A1     Oct. 20, 2022

Related U.S. Application Data

(63) Continuation of application No. 17/398,260, filed on Aug. 10, 2021, now Pat. No. 11,406,106, which is a continuation of application No. PCT/US2020/017909, filed on Feb. 12, 2020.

(60) Provisional application No. 62/940,013, filed on Nov. 25, 2019, provisional application No. 62/913,946, filed on Oct. 11, 2019, provisional application No. 62/804,588, filed on Feb. 12, 2019.

(51) Int. Cl.
| | | |
|---|---|---|
| A01N 59/00 | (2006.01) | |
| A01N 25/02 | (2006.01) | |
| A01N 37/02 | (2006.01) | |
| A01N 37/40 | (2006.01) | |
| A01P 1/00 | (2006.01) | |

(52) U.S. Cl.
CPC ............ *A01N 59/00* (2013.01); *A01N 25/02* (2013.01); *A01N 37/02* (2013.01); *A01N 37/40* (2013.01); *A01P 1/00* (2021.08)

(58) Field of Classification Search
CPC ........ A01N 59/00; A01N 25/02; A01N 37/02; A01N 37/40; A01P 1/00
See application file for complete search history.

(56) References Cited

U.S. PATENT DOCUMENTS

| | | |
|---|---|---|
| 4,477,438 A | 10/1984 | Willcockson et al. |
| 5,376,387 A | 12/1994 | Monticello |
| 5,387,605 A | 2/1995 | Beifuss et al. |
| 5,827,542 A | 10/1998 | Miner et al. |
| 6,024,986 A | 2/2000 | Hei |
| 6,043,209 A | 3/2000 | Micciche et al. |
| 6,096,348 A | 8/2000 | Miner et al. |
| 6,177,395 B1 | 1/2001 | Silvaggi et al. |
| 6,257,253 B1 | 7/2001 | Lentsch et al. |
| 6,302,968 B1 | 10/2001 | Baum et al. |
| 6,346,279 B1 | 2/2002 | Rochon |
| 6,686,324 B2 | 2/2004 | Ramirez et al. |
| 6,689,736 B2 | 2/2004 | Thomas et al. |
| 6,783,767 B2 | 8/2004 | Shroot et al. |
| 6,803,057 B2 | 10/2004 | Ramirez et al. |
| 6,841,090 B1 | 1/2005 | Serego Allighieri et al. |
| 6,908,628 B2 | 6/2005 | Herruzo Cabrera |
| 6,908,891 B2 | 6/2005 | Biering et al. |
| 7,354,604 B2 | 4/2008 | Ramirez et al. |
| 7,632,523 B2 | 12/2009 | Ramirez et al. |
| 7,658,953 B2 | 2/2010 | Bobbert |
| 7,678,753 B2 | 3/2010 | Maki et al. |
| 7,879,365 B2 | 2/2011 | Modak et al. |
| 8,048,930 B2 | 11/2011 | Bobbert |
| 8,236,357 B2 | 8/2012 | Bobbert |
| 8,246,906 B2 | 8/2012 | Hei et al. |
| 8,563,017 B2 | 10/2013 | Cunningham et al. |
| 8,591,958 B2 | 11/2013 | Omidbakhsh et al. |
| 8,637,085 B2 | 1/2014 | Ramirez et al. |
| 8,673,365 B2 | 3/2014 | Wang et al. |
| 8,808,755 B2 | 8/2014 | Omidbakhsh et al. |

(Continued)

FOREIGN PATENT DOCUMENTS

| | | |
|---|---|---|
| EP | 0351772 | 1/1990 |
| EP | 1027827 | 8/2000 |

(Continued)

OTHER PUBLICATIONS

Database WPI [Online]; May 2018 (May 2018), XP002798822, AN 2018-367469.
International Search Report and Written Opinion issued in Corresponding PCT Application No. PCT/US2020/017909, dated May 7, 2020.
Kondo et al., "Further Studies on the Lethal Effect of Long-Chain Fatty Acids on Mycobacteria" *J. Med. Sci. Biol.* 1976, 29, 25-37.

(Continued)

*Primary Examiner* — Trevor Love
(74) *Attorney, Agent, or Firm* — NORTON ROSE FULBRIGHT US LLP

(57) ABSTRACT

An aqueous-based disinfecting composition is disclosed. The composition can include hydrogen peroxide at a concentration of 0.1 to 0.9% w/w, caprylic acid, or a salt thereof, at a concentration of 0.1 to 1% w/w, salicylic acid, or a salt thereof at a concentration of 0.1 to 1% w/w, and water. The composition does not include or is substantially free of a volatile C1-C7 alcohol, and the pH of the composition is from about 0.1 to about 6, and the composition is capable of exhibiting mycobactericidal activity against mycobacteria on a surface when the composition is in contact with the mycobacteria for at least 1 minute.

21 Claims, No Drawings

(56) References Cited

U.S. PATENT DOCUMENTS

| | | |
|---|---|---|
| 8,822,719 B1 | 9/2014 | Li et al. |
| 8,865,196 B2 | 10/2014 | Omidbakhsh |
| 8,865,226 B2 | 10/2014 | Bobbert |
| 8,883,074 B2 | 11/2014 | Bobbert |
| 8,999,400 B2 | 4/2015 | Ramirez et al. |
| 9,044,403 B2 | 6/2015 | Shultz |
| 9,125,405 B2 | 9/2015 | Mariowe et al. |
| 9,198,935 B2 | 12/2015 | Omidbakhsh et al. |
| 9,233,180 B2 | 1/2016 | Omidbakhsh et al. |
| 9,241,483 B2 | 1/2016 | Golden et al. |
| 9,271,494 B2 | 3/2016 | Pedersen et al. |
| 9,445,600 B2 | 9/2016 | Bui et al. |
| 9,491,965 B2 | 11/2016 | Man et al. |
| 9,538,760 B2 | 1/2017 | Zhu et al. |
| 9,737,076 B2 | 8/2017 | Zhu et al. |
| 9,789,216 B2 | 10/2017 | Berentsveig et al. |
| 9,872,930 B2 | 1/2018 | Berentsveig et al. |
| 9,901,100 B2 | 2/2018 | Bui et al. |
| 10,450,535 B2 | 10/2019 | Ahmadpour |
| 10,455,838 B2 | 10/2019 | Burke et al. |
| 2002/0192297 A1 | 12/2002 | Ramirez et al. |
| 2005/0194421 A1 | 9/2005 | Smolinski et al. |
| 2006/0099237 A1 | 5/2006 | Modak et al. |
| 2006/0285995 A1 | 12/2006 | Hobbs et al. |
| 2009/0304608 A1 | 12/2009 | Cueman et al. |
| 2009/0324508 A1 | 12/2009 | Bobbert |
| 2012/0107415 A1 | 5/2012 | Lisowsky et al. |
| 2012/0171300 A1 | 7/2012 | Koenig et al. |
| 2014/0308162 A1 | 10/2014 | Lange et al. |
| 2014/0328941 A1 | 11/2014 | Bui et al. |
| 2015/0010646 A1 | 1/2015 | Tiekemeier et al. |
| 2015/0265666 A1 | 9/2015 | Modak et al. |
| 2015/0305342 A1 | 10/2015 | Burke et al. |
| 2015/0305343 A1 | 10/2015 | Burke et al. |
| 2015/0306266 A1 | 10/2015 | Burke et al. |
| 2015/0327554 A1 | 11/2015 | Berentsveig et al. |
| 2015/0373986 A1 | 12/2015 | Burke et al. |
| 2016/0074549 A1 | 3/2016 | Lei et al. |
| 2016/0135453 A1 | 5/2016 | Pedersen et al. |
| 2016/0295860 A1 | 10/2016 | Dagher et al. |
| 2017/0002299 A1 | 1/2017 | Holtz et al. |
| 2017/0173196 A1 | 6/2017 | Sherry et al. |
| 2017/0215427 A9 | 8/2017 | Burke et al. |
| 2017/0248522 A1 | 8/2017 | Li et al. |
| 2017/0321165 A1 | 11/2017 | Stokes et al. |
| 2017/0335253 A1 | 11/2017 | Man et al. |
| 2018/0007909 A1 | 1/2018 | Daigle |
| 2018/0141814 A1 | 5/2018 | Ahmadpour |
| 2018/0216045 A1 | 8/2018 | Salminen et al. |
| 2018/0235231 A1 | 8/2018 | Ahmadpour |
| 2018/0279610 A1 | 10/2018 | Ahmadpour |
| 2019/0297881 A1 | 10/2019 | Ahmadpour |

FOREIGN PATENT DOCUMENTS

| | | |
|---|---|---|
| JP | 09137192 | 5/1997 |
| WO | WO 98/18894 | 5/1989 |
| WO | WO 92/21239 | 12/1992 |
| WO | WO 2017/007416 | 1/2017 |
| WO | WO 2017/165408 | 9/2017 |
| WO | WO 2017/204727 | 11/2017 |
| WO | WO 2019/075176 | 4/2019 |

OTHER PUBLICATIONS

Kondo et al., "The Lethal Effect of Long-Chain Fatty Acids on Mycobacteria" *J. Med. Sci. Biol.* 1972, 25, 1-13.

Moore, Suzanne Louise. *The Mechanisms of Antibacterial Action of Some Nonionic Surfactants*. 1997. University of Brighton, Doctoral Thesis.

Saito et al., "Growth of Group IV Mycobacteria on Medium Containing Various Saturated and Unsaturated Fatty Acids" *Antimicrobial Agents and Chemotherapy* 1984, 26(2), 164-169.

Tiehm, Andreas "Degradation of Polycyclic Aromatic Hydrocarbons in the Presence of Synthetic Surfactants" *Applied and Environmental Microbiology* 1994, 60(1), 258-263.

ALCOHOL-FREE HYDROGEN PEROXIDE DISINFECTANT COMPOSITIONS AND METHODS OF USE THEREOF

CROSS-REFERENCE TO RELATED APPLICATION

This application is a continuation of U.S. application Ser. No. 17/398,260 filed Aug. 10, 2021, which is a continuation of International Application No. PCT/US2020/017909, filed Feb. 12, 2020, which claims the benefit of U.S. Provisional Application Nos. 62/804,588 filed Feb. 12, 2019, 62/913, 946 filed Oct. 11, 2019, and 62/940,013 filed Nov. 25, 2019. The contents of each of the referenced applications are incorporated into the present application by reference.

FIELD OF THE DISCLOSURE

The disclosure generally relates to surface disinfectants and more specifically to hard surface disinfectants containing hydrogen peroxide.

BACKGROUND

Surface disinfectant liquid products are used to disinfect or sterilize a variety of hard surfaces, for example, found in dental, hospital, clinical, and food handling/preparation environments. Many hard surface disinfectant liquid products currently on the market use volatile solvents in high concentrations (e.g., >20%) to achieve a broad spectrum antimicrobial effect including effectiveness against mycobacteria. However, these solvents contribute to an objectionable smell making these formulas difficult and hazardous to use in enclosed spaces. Still other formulas that contain low levels of active ingredients, such as hydrogen peroxide in aqueous solutions, use alcohols, such as volatile C1-C7 alcohols, to achieve a mycobactericidal effect. Such short chain (C1-C7) volatile alcohols include linear, branched, and aromatic alcohols, examples of which include methanol, ethanol, isopropanol, and benzyl alcohol. For example, the commercial product OPTIM® 1 (active ingredient 0.5% hydrogen peroxide) available from SciCan and manufactured by VIROX Technologies, Inc., which is covered under U.S. Pat. No. 7,632,523, is an example of a disinfectant that contains benzyl alcohol. These formulas claim a reduction in operational concerns due to the aqueous nature of such formulations. However, these formulas still exude a noticeably offensive scent indicating volatility of the alcohol constituents, which can raise concerns for chemically sensitive individuals. Thus, there exists a need for an alcohol-free surface disinfectant capable of achieving an antimicrobial effect, including a mycobactericidal effect, as good as or better than current hard surface disinfectant products containing alcohols.

SUMMARY

The present disclosure provides a solution to at least some of the aforementioned limitations and deficiencies in the art relating to surface disinfectants. In one aspect, the solution can be premised on the discovery of aqueous-based compositions that have low levels of hydrogen peroxide (e.g., 0.05% w/w to about 10% w/w) and are substantially or completely free of C1-C7 alcohols and/or volatile solvents. Notably, the compositions of the present disclosure, which can include a combination of: linear carboxylic acid(s); aromatic carboxylic acid(s); and one or more surfactants selected from sodium olefin sulfonate surfactants, C12 to C16 linear alkyl ether carboxylic acid(s), or sodium C8 to C16 alkyl sulfate surfactant(s); can exhibit broad spectrum antimicrobial activity and disinfecting properties against a variety of microorganisms despite not having C1-C7 alcohol or volatile solvents. This solves the problem of providing a nontoxic hard surface disinfectant while reducing compatibility issues and safety concerns normally associated with alcohol and volatile solvent containing disinfecting solutions. This is especially helpful in settings where fast acting, nontoxic, mycobacterial and tuberculocidal surface disinfection is needed but chemical exposure to short chain (C1-C7) alcohols and volatile solvents (by property, people, and/or equipment) is undesirable.

In one aspect, disclosed herein is an aqueous-based disinfecting composition comprising: (a) hydrogen peroxide at a concentration of about 0.05 to about 10% w/w; (b) one or more linear monocarboxylic acids with a carbon chain length of C1 to C4, or salt thereof, at a concentration of about 0.01 to about 5% w/w; (c) one or more linear monocarboxylic acids with a carbon chain length of C5 to C12, or salt thereof, at a concentration of about 0.01 to about 5% w/w; (d) an aromatic carboxylic acid, or salt thereof, wherein the aromatic carboxylic acid is at least one of benzoic acid or salt thereof, or a derivative of benzoic acid or salt thereof, at a concentration of about 0.01 to about 5% w/w; and (e) one or more sodium olefin sulfonate surfactants at a concentration of about 0.01 to about 5% w/w; wherein the pH of the composition is from about 0.1 to about 6.5.

In some embodiments, the composition does not contain or is substantially free of a volatile C1-C7 alcohol. In some embodiments, the pH of the composition is from about 0.8 to about 3, or from about 1 to 4, or from about 1 to 3. In some embodiments, the concentration of hydrogen peroxide is 0.1 to 0.9% w/w or 0.3 to 0.7% w/w. In some embodiments, the one or more linear monocarboxylic acids with a carbon chain length of C1 to C4, or salt thereof, is formic acid (C1), or salt thereof. In some embodiments, the one or more linear monocarboxylic acids with a carbon chain length of C5 to C12, or salt thereof is caprylic acid (C8) and/or capric acid (C10), or salt thereof. In some embodiments, the one or more linear monocarboxylic acids with a carbon chain length of C5 to C12, or salt thereof is caprylic acid (C8), or salt thereof. In some embodiments, the one or more linear monocarboxylic acids with a carbon chain length of C5 to C12, or salt thereof is caprylic acid (C8), or salt thereof. In some embodiments, the aromatic carboxylic acid, or salt thereof is a derivative of benzoic acid, or salt thereof. In some embodiments the derivative of benzoic acid, or salt thereof is salicylic acid, or salt thereof. In some embodiments, the one or more sodium olefin sulfonate surfactant is sodium C14-C16 olefin sulfonate. In some embodiments, the composition further comprises a sequestering or chelating agent. In some embodiments, the sequestering or chelating agent is etidronic acid (HEDP), or salt thereof. In some embodiments, the one or more linear monocarboxylic acids with a carbon chain length of C5 to C12, or salt thereof is caprylic acid (C8), or salt thereof; and the derivative of benzoic acid, or salt thereof, is salicylic acid, or salt thereof. In further embodiments, the concentration of caprylic acid (C8), or salt thereof is 0.1 to 1.0%; and the concentration of salicylic acid, or salt thereof is 0.1 to 0.5% w/w. In some embodiments, the composition further comprises a fragrance and/or a dye. In some embodiments, the fragrance is wintergreen oil. In some embodiments, the composition is capable of exhibiting antimicrobial or microbicidal activity against microorganisms on a surface when the composition is in contact with the microorganisms for at least about 1 minute, wherein the microorganisms are one or more of gram-positive bacteria, gram-negative bacteria, fungi, yeasts, molds, or mycobacteria, or any combination thereof.

In another aspect, disclosed herein is a composition comprising, consisting essentially of, or consisting of: (a) hydrogen peroxide at a concentration of 0.3 to 0.7% w/w; (b) formic acid, or salt thereof at a concentration of 0.01 to 5% w/w; (c) caprylic acid at a concentration of 0.01 to 5% w/w; (d) salicylic acid at a concentration of 0.01 to 5% w/w; (e) sodium C14-C16 olefin sulfonate at a concentration of 0.01 to 5% w/w, wherein the composition does not include or is substantially free of a volatile C1-C7 alcohol, and wherein the pH of the composition is from about 1 to about 3.

In some embodiments, the concentration of caprylic acid (C8), or salt thereof is 0.1 to 1.0% w/w, and the concentration of salicylic acid, or salt thereof is 0.1 to 0.5% w/w. In some embodiments, the composition optionally further comprises, consists essentially of, or consists of etidronic acid (HEDP) at a concentration of about 0.01 to about 5% w/w. In some embodiments, the composition optionally further comprises, consists essentially of, or consists of a fragrance and/or a dye. In some embodiments, the fragrance is wintergreen oil.

In another aspect, disclosed herein is an aqueous-based disinfecting composition comprising: (a) hydrogen peroxide at a concentration of about 0.05 to about 10% w/w; (b) one or more linear monocarboxylic acids with a carbon chain length of C1 to C4, or salt thereof, at a concentration of about 0.01 to about 5% w/w; (c) one or more linear monocarboxylic acids with a carbon chain length of C5 to C12, or salt thereof, at a concentration of about 0.01 to about 5% w/w; (d) an aromatic carboxylic acid, or salt thereof, wherein the aromatic carboxylic acid is at least one of benzoic acid or salt thereof, or a derivative of benzoic acid or salt thereof, at a concentration of about 0.01 to about 5% w/w; and (e) a surfactant selected from (I) one or more C12 to C16 linear alkyl ether carboxylic acids, or salt thereof, at a concentration of about 0.01 to about 5% w/w; and/or (II) one or more sodium C8 to C16 alkyl sulfate surfactants at a concentration of about 0.01 to about 5% w/w; wherein the pH of the composition is from about 0.1 to about 6.5.

In some embodiments, the composition does not contain or is substantially free of a volatile C1-C7 alcohol. In some embodiments, the pH is from about 0.8 to about 3, or from about 1 to 4, or from about 1 to 3. In some embodiments, the concentration of hydrogen peroxide is 0.1 to 0.9% w/w or 0.3 to 0.7% w/w. In some embodiments, the one or more linear monocarboxylic acids with a carbon chain length of C1 to C4, or salt thereof, is formic acid (C1), or salt thereof. In some embodiments, the one or more linear monocarboxylic acids with a carbon chain length of C5 to C12, or salt thereof is caprylic acid (C8) and/or capric acid (C10), or salt thereof. In some embodiments, the one or more linear monocarboxylic acids with a carbon chain length of C5 to C12, or salt thereof is caprylic acid (C8), or salt thereof. In some embodiments, the one or more linear monocarboxylic acids with a carbon chain length of C5 to C12, or salt thereof is caprylic acid (C8), or salt thereof. In some embodiments, the aromatic carboxylic acid, or salt thereof is a derivative of benzoic acid, or salt thereof. In some embodiments the derivative of benzoic acid, or salt thereof is salicylic acid, or salt thereof. In some embodiments, the one or more C12 to C16 linear alkyl ether carboxylic acids, or salt thereof, is laureth-5 carboxylic acid or sodium laureth-5 carboxylate. In some embodiments, the one or more sodium C8 to C16 alkyl sulfate surfactants is sodium lauryl sulfate. In some embodiments, the composition further comprises a sequestering or chelating agent. In some embodiments, the sequestering or chelating agent is etidronic acid (HEDP), or salt thereof. In some embodiments, the one or more linear monocarboxylic acids with a carbon chain length of C5 to C12, or salt thereof is caprylic acid (C8), or salt thereof; and the derivative of benzoic acid, or salt thereof, is salicylic acid, or salt thereof. In further embodiments, the concentration of caprylic acid (C8), or salt thereof is 0.1 to 1.0% w/w; and the concentration of salicylic acid, or salt thereof is 0.1 to 0.5% w/w. In some embodiments, the composition is capable of exhibiting antimicrobial or microbicidal activity against microorganisms on a surface when the composition is in contact with the microorganisms for at least about 1 minute, wherein the microorganisms are one or more of gram-positive bacteria, gram-negative bacteria, fungi, yeasts, molds or mycobacteria.

In another aspect, disclosed herein is a composition comprising, consisting essentially of, or consisting of: (a) hydrogen peroxide at a concentration of 0.3 to 0.7% w/w; (b) formic acid, or salt thereof at a concentration of 0.01 to 5% w/w; (c) caprylic acid at a concentration of 0.01 to 5% w/w; (d) salicylic acid at a concentration of 0.01 to 5% w/w; (e) a surfactant selected from (I) laureth-5 carboxylic acid or sodium laureth-5 carboxylate at a concentration of 0.01 to 5% w/w; and/or (II) sodium lauryl sulfate at a concentration of 0.01 to 5% w/w, wherein the composition does not include or is substantially free of a volatile C1-C7 alcohol, and wherein the pH of the composition is from about 1 to about 3.

In some embodiments, the concentration of caprylic acid (C8), or salt thereof is 0.1 to 1.0% w/w; and the concentration of salicylic acid, or salt thereof is 0.1 to 0.5% w/w. In some embodiments, the composition optionally further comprises, consists essentially of, or consists of etidronic acid (HEDP) at a concentration of about 0.01 to about 5% w/w. In some embodiments, the composition optionally further comprises, consists essentially of, or consists of phenylethyl alcohol. In some embodiments, the composition optionally further comprises, consists essentially of, or consists of a fragrance and/or a dye.

In another aspect, disclosed herein is an aqueous-based disinfecting composition comprising: (a) hydrogen peroxide at a concentration of about 0.05 to about 10% w/w; (b) one or more linear monocarboxylic acids with a carbon chain length of C1 to C4, or salt thereof, at a concentration of about 0.01 to about 5% w/w; (c) one or more linear monocarboxylic acids with a carbon chain length of C5 to C12, or salt thereof, at a concentration of about 0.01 to about 5% w/w; (d) an aromatic carboxylic acid, or salt thereof, wherein the aromatic carboxylic acid is at least one of benzoic acid or salt thereof, or a derivative of benzoic acid or salt thereof, at a concentration of about 0.01 to about 5% w/w; and (e) a surfactant selected from (I) one or more C12 to C16 linear alkyl ether carboxylic acids, or salt thereof, at a concentration of about 0.01 to about 5% w/w; (II) one or more sodium C8 to C16 alkyl sulfate surfactants at a concentration of about 0.01 to about 5% w/w; and/or (III) one or more sodium olefin sulfonate surfactants at a concentration of about 0.01 to about 5% w/w; wherein the pH of the composition is from about 0.1 to about 6.5.

In some embodiments, the composition does not contain or is substantially free of a volatile C1-C7 alcohol. In some embodiments, the pH is from about 0.8 to about 3, or from about 1 to 4, or from about 1 to 3. In some embodiments, the concentration of hydrogen peroxide is 0.1 to 0.9% w/w or 0.3 to 0.7% w/w. In some embodiments, the one or more linear monocarboxylic acids with a carbon chain length of C1 to C4, or salt thereof, is formic acid (C1), or salt thereof. In some embodiments, the one or more linear monocarboxylic acids with a carbon chain length of C5 to C12, or salt thereof is caprylic acid (C8) and/or capric acid (C10), or salt thereof. In some embodiments, the one or more linear monocarboxylic acids with a carbon chain length of C5 to C12, or salt thereof is caprylic acid (C8), or salt thereof. In some embodiments, the one or more linear monocarboxylic acids with a carbon chain length of C5 to C12, or salt thereof is caprylic acid (C8), or salt thereof. In some embodiments, the aromatic carboxylic acid, or salt thereof is a derivative of benzoic acid, or salt thereof. In some embodiments the derivative of benzoic acid, or salt thereof is salicylic acid, or salt thereof. In some embodiments, the one or more C12 to C16 linear alkyl ether carboxylic acids, or salt thereof, is laureth-5 carboxylic acid or sodium laureth-5 carboxylate. In some embodiments, the one or more sodium C8 to C16 alkyl sulfate surfactants is sodium lauryl sulfate. In some embodiments, the one or more sodium olefin sulfonate surfactant is sodium C14-C16 olefin sulfonate. In some embodiments, the composition further comprises a sequestering or chelating agent. In some embodiments, the sequestering or chelating agent is etidronic acid (HEDP), or salt thereof. In some embodiments, the one or more linear monocarboxylic acids with a carbon chain length of C5 to C12, or salt thereof is caprylic acid (C8), or salt thereof; and the derivative of benzoic acid, or salt thereof, is salicylic acid, or salt thereof. In further embodiments, the concentration of caprylic acid (C8), or salt thereof is 0.1 to 1.0% w/w; and the concentration of salicylic acid, or salt thereof is 0.1 to 0.5% w/w. In some embodiments, the composition further comprises a fragrance and/or a dye. In some embodiments, the fragrance is wintergreen oil. In some embodiments, the composition further comprises phenethyl alcohol. In some embodiments, the composition is capable of exhibiting antimicrobial or microbicidal activity against microorganisms on a surface when the composition is in contact with the microorganisms for at least about 1 minute, wherein the microorganisms are one or more of gram-positive bacteria, gram-negative bacteria, fungi, yeasts, molds or mycobacteria.

In another aspect, disclosed is a method of disinfecting or sterilizing a surface, the method comprising contacting an aqueous-based disinfecting composition of the present disclosure with the surface, and allowing the composition to remain in contact with the surface for a period of time thereby disinfecting or sterilizing the surface. In some embodiments, the contact time is at least about 30 seconds, at least about 1 minute, at least about 1.5 minutes, at least about 2 minutes, at least about 3 minutes, at least about 4 minutes, or at least about 5 minutes. In some instances, the contact time is at least about 30 seconds to about 5 minutes, at least about 1 minute to about 5 minutes, or about 2 minutes to about 5 minutes. In some embodiments, the contact time can be more that 5 minutes (e.g., 6, 7, 8, 9, 10, 15, 20, 30, 45, or 60 minutes, or more, or any range or time therein). In one particular aspect, the contact time is at least about 30 seconds. In another particular aspect, the contact time is at least about 1 minute.

Also, disclosed in the context of the present disclosure are the following embodiments 1 to 55:

Embodiment 1 is an aqueous-based disinfecting composition comprising: (a) hydrogen peroxide at a concentration of about 0.05 to about 10% w/w, (b) one or more linear monocarboxylic acids with a carbon chain length of C1 to C4, or salt thereof, at a concentration of about 0.01 to about 5% w/w; (c) one or more linear monocarboxylic acids with a carbon chain length of C5 to C12, or salt thereof, at a concentration of about 0.01 to about 5% w/w; (d) an aromatic carboxylic acid, or salt thereof, wherein the aromatic carboxylic acid is at least one of benzoic acid or salt thereof, or a derivative of benzoic acid or salt thereof, at a concentration of about 0.01 to about 5% w/w; and (e) one or more sodium olefin sulfonate surfactants at a concentration of about 0.01 to about 5% w/w; wherein the composition does not contain or is substantially free of a volatile C1-C7 alcohol, and wherein the pH of the composition is from about 0.1 to about 6.5.

Embodiment 2 is the composition of embodiment 1, wherein the concentration of hydrogen peroxide is 0.1 to 0.9% w/w.

Embodiment 3 is the composition of any of one of embodiments 1 or 2, wherein the concentration of hydrogen peroxide is 0.3 to 0.7% w/w.

Embodiment 4 is the composition of any one of embodiments 1 to 3, wherein the one or more linear monocarboxylic acids with a carbon chain length of C1 to C4, or salt thereof, is formic acid (C1), or salt thereof.

Embodiment 5 is the composition of any one of embodiments 1 to 4, wherein the one or more linear monocarboxylic acids with a carbon chain length of C5 to C12, or salt thereof is caprylic acid (C8) and/or capric acid (C10), or salt thereof.

Embodiment 6 is the composition of embodiment 5, wherein the one or more linear monocarboxylic acids with a carbon chain length of C5 to C12, or salt thereof is caprylic acid (C8), or salt thereof.

Embodiment 7 is the composition of any one of embodiments 1 to 6, wherein the aromatic carboxylic acid, or salt thereof is a derivative of benzoic acid, or salt thereof.

Embodiment 8 is the composition of embodiment 7, wherein the derivative of benzoic acid, or salt thereof, is salicylic acid, or salt thereof.

Embodiment 9 is the composition of anyone of embodiments 1 to 8, wherein the sodium olefin sulfonate surfactant is sodium C14-C16 olefin sulfonate.

Embodiment 10 is the composition of any one of embodiments 1 to 9, wherein the composition further comprises a sequestering or chelating agent.

Embodiment 11 is the composition of embodiment 10, wherein the sequestering or chelating agent is etidronic acid (HEDP), or salt thereof.

Embodiment 12 is the composition of any one of embodiments 1 to 11, wherein the one or more linear monocarboxylic acids with a carbon chain length of C5 to C12, or salt thereof is caprylic acid (C8), or salt thereof; and wherein the derivative of benzoic acid, or salt thereof, is salicylic acid, or salt thereof.

Embodiment 13 is the composition of embodiment 12 wherein the concentration of caprylic acid (C8), or salt thereof is 0.1 to 1.0% w/w, and the concentration of salicylic acid, or salt thereof is 0.1 to 0.5% w/w.

Embodiment 14 is the composition of any one of embodiments 1 to 13, wherein the composition further comprises a fragrance and/or dye.

Embodiment 15 is the composition of embodiment 14, wherein the fragrance is wintergreen oil.

Embodiment 16 is the composition of any one of embodiments 1 to 15, wherein the pH of the composition is from about 1 to about 4, or from about 1 to about 3.

Embodiment 17 is the composition of any one of embodiments 1 to 16, wherein the composition is capable of exhibiting antimicrobial or bactericidal activity against microorganisms on a surface when the composition is in contact with the microorganisms for at least about 1 minute, wherein the microorganisms are one or more of gram-positive bacteria, gram-negative bacteria, fungi, yeasts, molds, or mycobacteria.

Embodiment 18 is the composition of any one of embodiments 1 to 17, comprising at least 95% w/w water, or at least 97% w/w water.

Embodiment 19 is an aqueous-based disinfecting composition consisting essentially of: (a) hydrogen peroxide at a concentration of 0.3 to 0.7% w/w, (b) formic acid, or salt thereof at a concentration of 0.01 to 5% w/w, (c) caprylic acid, or salt thereof at a concentration of 0.01 to 5% w/w, (d) salicylic acid, or salt thereof at a concentration of 0.01 to 5% w/w, (e) sodium C14-C16 olefin sulfonate at a concentration of 0.01 to 5% w/w, wherein the composition does not include or is substantially free of a volatile C1-C7 alcohol, and wherein the pH of the composition is from about 1 to about 3.

Embodiment 20 is the composition of embodiment 19, wherein, the concentration of caprylic acid (C8), or salt thereof is 0.1 to 1.0% w/w, and the concentration of salicylic acid, or salt thereof is 0.1 to 0.5% w/w.

Embodiment 21 is the composition of any one of embodiments 19 or 20, wherein the composition optionally further consists essentially of etidronic acid (HEDP) at a concentration of about 0.01 to about 5% w/w.

Embodiment 22 is the composition of any one of embodiments 19 to 21, wherein the composition optionally further consists essentially of a fragrance and/or a dye.

Embodiment 23 is the composition of embodiment 22, wherein the fragrance is wintergreen oil.

Embodiment 24 is the composition of any one of embodiments 19 to 23, comprising at least 95% w/w water, or at least 97% w/w water.

Embodiment 25 is a method of disinfecting or sterilizing a surface, the method comprising: contacting the composition of any one of embodiments 1 to 24 with the surface, and allowing the composition to remain in contact with the surface for a period of time thereby disinfecting or sterilizing the surface.

Embodiment 26 is the method of embodiment 25, wherein the period of time is at least about 1 minute.

Embodiment 27 is the method of any one of embodiments 25 or 26, wherein the surface is at least a portion of the surface of medical equipment, medical devices, medical tools, or medical instruments.

Embodiment 28 is an aqueous-based disinfecting composition comprising: (a) hydrogen peroxide at a concentration of about 0.05 to about 10% w/w, (b) one or more linear monocarboxylic acids with a carbon chain length of C1 to C4, or salt thereof, at a concentration of about 0.01 to about 5% w/w; (c) one or more linear monocarboxylic acids with a carbon chain length of C5 to C12, or salt thereof, at a concentration of about 0.01 to about 5% w/w; (d) an aromatic carboxylic acid, or salt thereof, wherein the aromatic carboxylic acid is at least one of benzoic acid or salt thereof, or a derivative of benzoic acid or salt thereof, at a concentration of about 0.01 to about 5% w/w; and (e) a surfactant selected from (I) one or more C12 to C16 linear alkyl ether carboxylic acids, or salt thereof, at a concentration of about 0.01 to about 5% w/w; and/or (II) one or more sodium C8 to C16 alkyl sulfate surfactants at a concentration of about 0.01 to about 5% w/w; wherein the composition does not contain or is substantially free of a volatile C1-C7 alcohol, and wherein the pH of the composition is from about 0.1 to about 6.5.

Embodiment 29 is the composition of embodiment 28, wherein the concentration of hydrogen peroxide is 0.1 to 0.9% w/w.

Embodiment 30 is the composition of any of one of embodiments 28 or 29, wherein the concentration of hydrogen peroxide is 0.3 to 0.7% w/w.

Embodiment 31 is the composition of any one of embodiments 28 to 30, wherein the one or more linear monocarboxylic acids with a carbon chain length of C1 to C4, or salt thereof, is formic acid (C1), or salt thereof.

Embodiment 32 is the composition of any one of embodiments 28 to 31, wherein the one or more linear monocarboxylic acids with a carbon chain length of C5 to C12, or salt thereof is caprylic acid (C8) and/or capric acid (C10), or salt thereof.

Embodiment 33 is the composition of embodiment 32, wherein the one or more linear monocarboxylic acids with a carbon chain length of C5 to C12, or salt thereof is caprylic acid (C8), or salt thereof.

Embodiment 34 is the composition of any one of embodiments 28 to 33, wherein the aromatic carboxylic acid, or salt thereof is a derivative of benzoic acid, or salt thereof.

Embodiment 35 is the composition of embodiment 34, wherein the derivative of benzoic acid, or salt thereof, is salicylic acid, or salt thereof.

Embodiment 36 is the composition of any one of embodiments 28 to 35, wherein the one or more C12 to C16 linear alkyl ether carboxylic acids, or salt thereof, is laureth-5 carboxylic acid or sodium laureth-5 carboxylate.

Embodiment 37 is the composition of any one of embodiments 28 to 36, wherein the one or more sodium C8 to C16 alkyl sulfate surfactants is sodium lauryl sulfate.

Embodiment 38 is the composition of any one of embodiments 28 to 37, wherein the composition further comprises a sequestering or chelating agent.

Embodiment 39 is the composition of embodiment 38, wherein the sequestering or chelating agent is etidronic acid (HEDP), or salt thereof.

Embodiment 40 is the composition of any one of embodiments 28 to 39, wherein the one or more linear monocarboxylic acids with a carbon chain length of C5 to C12, or salt thereof is caprylic acid (C8), or salt thereof; and wherein the derivative of benzoic acid, or salt thereof, is salicylic acid, or salt thereof.

Embodiment 41 is the composition of embodiment 40 wherein the concentration of caprylic acid (C8), or salt thereof is 0.1 to 1.0% w/w, and the concentration of salicylic acid, or salt thereof is 0.1 to 0.5% w/w.

Embodiment 42 is the composition of any one of embodiments 28 to 41, wherein the pH of the composition is from about 1 to about 4, or from about 1 to about 3.

Embodiment 43 is the composition of any one of embodiments 28 to 42, wherein the composition further comprises phenethyl alcohol.

Embodiment 44 is the composition of any one of embodiments 28 to 43, wherein the composition further comprises a fragrance and/or a dye.

Embodiment 45 is the composition of any one of embodiments 28 to 44, wherein the composition is capable of exhibiting antimicrobial or bactericidal activity against microorganisms on a surface when the composition is in contact with the microorganisms for at least about 1 minute, wherein the microorganisms are one or more of gram-positive bacteria, gram-negative bacteria, fungi, yeasts, molds, or mycobacteria.

Embodiment 46 is the composition of any one of embodiments 28 to 45, comprising at least 95% w/w water, or at least 97% w/w water.

Embodiment 47 is an aqueous-based disinfecting composition consisting essentially of: (a) hydrogen peroxide at a concentration of 0.3 to 0.7% w/w, (b) formic acid, or salt thereof at a concentration of 0.01 to 5% w/w, (c) caprylic acid, or salt thereof at a concentration of 0.01 to 5% w/w, (d) salicylic acid, or salt thereof at a concentration of 0.01 to 5% w/w, and (e) a surfactant selected from (I) laureth-5 carboxylic acid or sodium laureth-5 carboxylate at a concentration of 0.01 to 5% w/w, and/or (II) sodium lauryl sulfate at a concentration of 0.01 to 5% w/w, wherein the composition does not include or is substantially free of a volatile C1-C7 alcohol, and wherein the pH of the composition is from about 1 to about 3.

Embodiment 48 is the composition of embodiment 47, wherein, the concentration of caprylic acid (C8), or salt thereof is 0.1 to 1.0% w/w, and the concentration of salicylic acid, or salt thereof is 0.1 to 0.5% w/w.

Embodiment 49 is the composition of any one of embodiments 47 or 48, wherein the composition optionally further consists essentially of etidronic acid (HEDP) at a concentration of about 0.01 to about 5% w/w.

Embodiment 50 is the composition of any one of embodiments 47 to 49, wherein the composition optionally further consists essentially of phenethyl alcohol at a concentration of 0.1 to 1% w/w.

Embodiment 51 is the composition of any one of embodiments 47 to 50, wherein the composition optionally further consists essentially of a fragrance and/or a dye.

Embodiment 52 is the composition of any one of embodiments 47 to 51, comprising at least 95% w/w water, or at least 97% w/w water.

Embodiment 53 is a method of disinfecting or sterilizing a surface, the method comprising: contacting the composition of any one of embodiments 28 to 53 with the surface, and allowing the composition to remain in contact with the surface for a period of time thereby disinfecting or sterilizing the surface.

Embodiment 54 is the method of embodiment 53, wherein the period of time is at least about 1 minute.

Embodiment 55 is the method of any one of embodiments 53 or 54, wherein the surface is at least a portion of the surface of medical equipment, medical devices, medical tools, or medical instruments.

Also disclosed in the context of the present disclosure are the aqueous-based disinfecting compositions described in Tables 1, 21, and/or 24 of the Examples, which are incorporated into this paragraph by reference.

In another embodiment, there is disclosed an aqueous-based disinfecting composition comprising (a) hydrogen peroxide at a concentration of about 0.05 to about 10% w/w and (b) at least one of, at least two of, at least three of, at least four of, or all five of: (i) one or more linear monocarboxylic acids with a carbon chain length of C1 to C4, or salt thereof, at a concentration of about 0.01 to about 5% w/w; (ii) one or more linear monocarboxylic acids with a carbon chain length of C5 to C12, or salt thereof, at a concentration of about 0.01 to about 5% w/w; (iii) an aromatic carboxylic acid, or salt thereof, wherein the aromatic carboxylic acid is at least one of benzoic acid or salt thereof, or a derivative of benzoic acid or salt thereof, at a concentration of about 0.01 to about 5% w/w; (iv) one or more C12 to C16 linear alkyl ether carboxylic acids, or salt thereof, at a concentration of about 0.01 to about 5% w/w; (v) one or more sodium C8 to C16 alkyl sulfate surfactants at a concentration of about 0.01 to about 5% w/w, and/or (vi) one or more sodium olefin sulfonate surfactants at a concentration of about 0.01 to about 5% w/w; wherein the composition does not contain or is substantially free of a volatile C1-C7 alcohol, and wherein the pH of the composition is from about 0.1 to about 6.5. In some instances, the composition comprises, consists essentially of, or consists of (a) and (i). In some instances, the composition comprises, consists essentially of, or consists of (a) and (ii). In some instances, the composition comprises, consists essentially of, or consists of (a) and (iii). In some instances, the composition comprises, consists essentially of, or consists of (a) and (iv). In some instances, the composition comprises, consists essentially of, or consists of (a) and (v). In some instances, the composition comprises, consists essentially of, or consists of (a), (ii), and (iii). Optionally, any of the compositions above can also include a sequestering or chelating agent (e.g., etidronic acid (HEDP)), or salt thereof; a fragrance; and a dye.

As used herein, the terms "aqueous" or "aqueous-based" with respect to a composition means a composition with water being the component with the greatest concentration level in the composition. For example, an aqueous or aqueous-based disinfecting composition can include greater than 50% w/w, at least 60% w/w, at least 70% w/w, at least 80% w/w, at least 90% w/w, at least 91% w/w, at least 92% w/w, at least 93% w/w, at least 94% w/w, at least 95% w/w, at least 96% w/w, at least 97% w/w, at least 98% w/w, or at least 99% w/w, or any range therein, of water. In some preferred aspects, an aqueous or aqueous-based disinfecting composition of the present disclosure can include at least 90% w/w, more preferably at least 95% w/w, or even more preferably at least 97% w/w, or 97% w/w to 99% w/w water. In one instance, an aqueous or aqueous-based disinfecting composition of the present disclosure can include 97% w/w to 98.5% w/w water.

As used herein, the terms "about" or "approximately" are defined as being close to as understood by one of ordinary skill in the art, and in one non-limiting embodiment the terms are defined to be within 10%, preferably within 5%, more preferably within 1%, and most preferably within 0.5%.

As used herein, the terms "do not contain" or "does not contain" mean that an indicated material is not added as an ingredient/component to a composition and is excluded from a composition.

As used herein, the term "substantially free of" means the presence of less than about 0.1% w/w, or less than about 0.08% w/w, or less than about 0.05% w/w, or less than about 0.01% w/w of an indicated material in a composition.

As used herein, percentage values can represent various percentage types, e.g. weight percentage, volume percentage, etc. As used herein, the terms "% w/w" or "wt. %" refers to a weight percentage of a component based on the total weight of material (e.g. a composition) that includes the component. In a non-limiting example, 10 grams of a component in 100 grams of a composition is 10% w/w of the component in the total weight of composition. As used herein, the terms "% v/v" or "vol. %" refers to a volume percentage of a component based on the total volume of material (e.g. a composition) that includes the component. In a non-limiting example, 10 mL of a component in 100 mL of a composition is 10% v/v of the component in the total volume of composition. As used herein, the term "% w/v" refers to a weight percentage of a component based on the total volume of material (e.g. a composition) that includes the component. In a non-limiting example, 10 grams of a component in 100 mL of a composition is 10% w/v of the component in the total volume of composition. As used herein, the term "% v/w" refers to a volume percentage of a component based on the total weight of material (e.g. a composition) that includes the component. In a non-limiting example, 10 mL of a component in 100 grams of a composition is 10% v/w of the component in the total weight of the composition. When the lower limit value of a given percentage range does not include the % symbol and/or the percentage type (e.g. w/w, v/v, etc.), then the percentage type for the lower limit value is the same as for the upper limit value of the given percentage range. For example, the percentage range of "0.01 to 0.5% w/w" means "0.01% w/w to 0.5% w/w."

As used herein, the terms "antimicrobial," "antimicrobial activity," "antimicrobial efficacy," "antimicrobial effect," and "antimicrobial effectiveness" mean accomplishing at least one of the following: (a) destruction of microorganisms (complete kill), (b) growth reduction of microorganisms, or (c) growth inhibition of microorganisms.

As used herein, the terms "antibacterial," "antibacterial activity," "antibacterial effect/efficacy/effectiveness," "antifungal," "antifungal activity", "antifungal efficacy/effectiveness," "antiviral," "antiviral activity", "antiviral effect/efficacy/effectiveness," "antimycobacterial," "antimycobacterial activity," and "antimycobacterial effect/efficacy/effectiveness" mean accomplishing at least one of the following: (a) destruction of the respective microorganism (complete kill), (b) growth reduction of the respective microorganism, or (c) growth inhibition of the respective microorganism.

As used herein, the terms "microbicidal," "microbicidal activity," "microbicidal effect," "microbicidal efficacy," and "microbicidal effectiveness" mean accomplishing the destruction of microorganisms (complete kill).

As used herein, the terms "bactericidal," "fungicidal," "viricidal," "mycobactericidal" mean the destruction of the respective microorganism (complete kill).

As used herein, the terms "sporicidal," "sporicidal activity," and "sporicidal efficacy/effectiveness" mean the destructions of spores (complete kill).

As used herein, the terms "disinfect," "disinfecting," and "disinfection" mean accomplishing at least one of the following: (a) destruction of microorganisms (complete kill), (b) growth reduction of microorganisms, or (c) growth inhibition of microorganisms on a surface.

As used herein, the terms "sterilize," "sterilizing," and "sterilization" mean the destruction of microorganisms (complete kill) on a surface.

As used herein, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

As used herein, the use of the word "a" or "an" when used in conjunction with the terms "comprising," "having," "including," or "containing" (or any variations of these words) may mean "one," but it is also consistent with the meaning of "one or more," "at least one," and "one or more than one."

The compositions and methods for their use can "comprise," "consist essentially of," or "consist of" any of the ingredients or steps disclosed throughout the specification. With respect to the transitional phrase "consisting essentially of," in one non-limiting aspect, a basic and novel characteristic of the disinfectant compositions disclosed herein is to provide broad spectrum disinfecting properties against microorganisms including gram-positive bacteria, gram-negative bacteria, fungi including yeasts and molds, and mycobacteria substantially free of or without the inclusion of alcohols or other ingredients that contribute to the antimicrobial efficacy of the compositions.

It is contemplated that any embodiment discussed in this specification can be implemented with respect to any method or composition of the disclosure, and vice versa. Furthermore, compositions of the disclosure can be used to achieve methods of the disclosure.

Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

DETAILED DESCRIPTION

Disclosed herein are fast-acting, C1-C7 alcohol-free, aqueous-based disinfectant compositions containing hydrogen peroxide, which are useful for the disinfection a variety of surfaces and exhibit broad spectrum antimicrobial activity and/or microbicidal activity against a variety of microorganisms.

Compositions

In some aspects, the compositions disclosed herein contain the following components in water:
  an oxidizing agent such as hydrogen peroxide;
  one or more linear monocarboxylic acids with a carbon chain length of C1 to C4, or salt thereof; one or more linear monocarboxylic acids with a carbon chain length of C5 to C12, or salt thereof;
  an aromatic carboxylic acid, or salt thereof, selected from benzoic acid and/or one or more derivatives of benzoic acid, or salt thereof;
  and a surfactant selected from one or more C12 to C16 linear alkyl ether carboxylic acids, or salt thereof; one or more sodium C8 to C16 alkyl sulfate surfactants; and/or one or more sodium olefin sulfonate surfactants.

In some aspects, the compositions of the present disclosure do not contain or are substantially free of volatile C1-C7 alcohols including linear, branched, and aromatic alcohols. Non-limiting examples of these alcohols include methanol, ethanol, isopropanol, and benzyl alcohol. As used herein, a volatile compound (e.g., alcohol or solvent) is defined as a compound that evaporates more than 95% by weight within 6 months under ambient (20° to 30° C.) conditions with no discernible air flow. See Vo et al., Nonvolatile, semivolatile, or volatile: Redefining volatile for volatile organic compounds, Journal of the Air & Waste Management Association, 64:6, 661-669, 2014, herein incorporated by reference. For example, as per Vo et al., isopropyl alcohol and benzyl alcohol are volatile compounds since isopropyl alcohol evaporates completely within 2 days and benzyl alcohol fully evaporates in 2 weeks. Surprisingly, the compositions of the present disclosure have exhibited antimicrobial and microbicidal activity against mycobacteria without the inclusion of volatile C1-C7 alcohols. Additionally, and also surprisingly, the compositions of the present disclosure have exhibited antimicrobial and microbicidal activity across a broad spectrum of microorganisms without the inclusion of peracids or percarboxylic acids such as peracetic acid. In some embodiments, the compositions do not contain or are substantially free of volatile C1-C7 alcohols. In some embodiments, the compositions do not contain or are substantially free of methanol, ethanol, and/or isopropanol. In some embodiments, the compositions do not contain or are substantially free of benzyl alcohol. In some embodiments, the compositions do not contain or are substantially free of volatile solvents. In some embodiments, the compositions of the present disclosure do not contain or are substantially free of glycol ether solvents. Non-limiting examples of glycol ether solvents include tripropylene glycol methyl ether, tripropylene glycol n-butyl ether, polyethylene glycol phenyl ether, dipropylene glycol methyl ether, propylene glycol n-propyl ether, propylene glycol monomethyl ether, dipropylene glycol monopropyl ether, propylene glycol mono n-butyl ether, dipropylene glycol mono n-butyl ether, dipropylene glycol dimethyl ether, diethylene glycol mono-methyl ether, diethylene glycol monoethyl ether, ethylene glycol monopropyl ether, ethylene glycol monobutyl ether, diethylene glycol monobutyl ether, ethylene glycol monohexyl ether, diethylene glycol monohexyl ether, and ethylene glycol phenyl ether.

The compositions of the present disclosure can contain an oxidizing agent. The preferred oxidizing agent is hydrogen peroxide. Hydrogen peroxide is used an antimicrobial agent active ingredient and is effective in the compositions in combination with other ingredients that contribute to the overall antimicrobial activity of the composition. Hydrogen peroxide (CAS No. 7722-84-1) is commercially available in aqueous solutions at various concentrations, e.g., 30%, 35%, and 50% solutions. The hydrogen peroxide can contain trace amounts of stabilizers. The desired concentration of the hydrogen peroxide in the compositions disclosed herein can be accomplished by dilution of the concentrated solutions. The concentration of hydrogen peroxide in the compositions can be from about 0.05 to about 10% w/w. In some embodiments, the concentration of hydrogen peroxide in the compositions is 0.05 to 10% w/w, or 0.05 to 5% w/w, or 0.05 to 4% w/w, or 0.05 to 3% w/w, or 0.05 to 2% w/w, or 0.05 to 1% w/w, or 0.05 to 0.9% w/w, or 0.05 to 0.8% w/w, or 0.05 to 0.7% w/w, or 0.05 to 0.6% w/w, or 0.05 to 0.5% w/w, or 0.1 to 10% w/w, or 0.1 to 5% w/w, or 0.1 to 4% w/w, or 0.1 to 3% w/w, or 0.1 to 2% w/w, or 0.1 to 1% w/w, or 0.1 to 0.9% w/w, or 0.1 to 0.8% w/w, or 0.1 to 0.7% w/w, or 0.1 to 0.6% w/w, or 0.1 to 0.5% w/w, or 0.1 to 0.4% w/w, or 0.1 to 0.3% w/w, or 0.2 to 10% w/w, or 0.2 to 5% w/w, or 0.2 to 4% w/w, or 0.2 to 3% w/w, or 0.2 to 2% w/w, or 0.2 to 1% w/w, or 0.2 to 0.9% w/w, or 0.2 to 0.8% w/w, or 0.2 to 0.7% w/w, or 0.2 to 0.6% w/w, or 0.2 to 0.5% w/w, 0.2 to 0.4% w/w, or 0.2 to 0.3% w/w, or 0.3 to 10% w/w, or 0.3 to 5% w/w, or 0.3 to 4% w/w, or 0.3 to 3% w/w, or 0.3 to 2% w/w, or 0.3 to 1% w/w, or 0.3 to 0.9% w/w, or 0.3 to 0.8% w/w, or 0.3 to 0.7% w/w, or 0.3 to 0.6% w/w, or 0.3 to 0.5% w/w, or 0.4 to 10% w/w, or 0.4 to 5% w/w, or 0.4 to 4% w/w, or 0.4 to 3% w/w, or 0.4 to 2% w/w, or 0.4 to 1% w/w, or 0.4 to 0.9% w/w, or 0.4 to 0.8% w/w, or 0.4 to 0.7% w/w, or 0.4 to 0.6% w/w, or 0.4 to 0.5% w/w, or 0.5 to 10% w/w, or 0.5 to 5% w/w, or 0.5 to 4% w/w, or 0.5 to 3% w/w, or 0.5 to 2% w/w, or 0.5 to 1% w/w, or 0.5 to 0.9% w/w, or 0.5 to 0.8% w/w, or 0.5 to 0.7% w/w, or 0.5 to 0.6% w/w, or 0.5% w/w, or about 0.5% w/w.

The compositions of the present disclosure can include one or more linear monocarboxylic acids with a carbon chain length of C1 to C4, or salt thereof, and also one or more linear monocarboxylic acids with a carbon chain length of C5 to C12, or salt thereof. These carboxylic acids contribute to the overall antimicrobial activity of the compositions. Examples of linear C1 to C4 monocarboxylic acids are formic acid (C1), acetic acid (C2), propionic acid (C3) and butyric acid (C4). Formic acid (CAS No. 64-18-6), acetic acid (CAS No. 64-19-7), propionic acid (CAS No. 79-09-4), and butyric acid (CAS No. 107-92-6) are all available commercially from Sigma-Aldrich. In some embodiments, the linear C1 to C4 monocarboxylic acid, or salt thereof, in the composition is formic acid (C1), or salt thereof. The total concentration of the one or more linear C1 to C4 monocarboxylic acid, or salt thereof, in the compositions can be from about 0.01 to about 5% w/w. In some embodiments, the total concentration of the one or more linear C1 to C4 monocarboxylic acids, or salt thereof, in the compositions is 0.01 to 5% w/w, or 0.01 to 4% w/w, or 0.01 to 3% w/w, or 0.01 to 2% w/w, or 0.01 to 1% w/w, or 0.01 to 0.9% w/w, or 0.01 to 0.8% w/w, or 0.01 to 0.7% w/w, or 0.01 to 0.6% w/w, or 0.01 to 0.5% w/w, or 0.05 to 5% w/w, or 0.05 to 4% w/w, or 0.05 to 3% w/w, or 0.05 to 2% w/w, or 0.05 to 1% w/w, or 0.05 to 0.9% w/w, or 0.05 to 0.8% w/w, or 0.05 to 0.7% w/w, or 0.05 to 0.6% w/w, or 0.05 to 0.5% w/w, or 0.1 to 5% w/w, or 0.1 to 4% w/w, or 0.1 to 3% w/w, or 0.1 to 2% w/w, or 0.1 to 1% w/w, or 0.1 to 0.9% w/w, or 0.1 to 0.8% w/w, or 0.1 to 0.7% w/w, or 0.1 to 0.6% w/w, or 0.1 to 0.5% w/w, or 0.2 to 5% w/w, or 0.2 to 4% w/w, or 0.2 to 3% w/w, or 0.2 to 2% w/w, or 0.2 to 1% w/w, or 0.2 to 0.9% w/w, or 0.2 to 0.8% w/w, or 0.2 to 0.7% w/w, or 0.2 to 0.6% w/w, or 0.2 to 0.5% w/w, or 0.3 to 5% w/w, or 0.3 to 4% w/w, or 0.3 to 3% w/w, or 0.3 to 2% w/w, or 0.3 to 1% w/w, or 0.3 to 0.9% w/w, or 0.3 to 0.8% w/w, or 0.3 to 0.7% w/w, or 0.3 to 0.6% w/w, or 0.3 to 0.5% w/w, or 0.4 to 5% w/w, or 0.4 to 4% w/w, or 0.4 to 3% w/w, or 0.4 to 2% w/w, or 0.4 to 1% w/w, or 0.4 to 0.9% w/w, or 0.4 to 0.8% w/w, or 0.4 to 0.7% w/w, or 0.4 to 0.6% w/w, or 0.4 to 0.5% w/w, or 0.5 to 5% w/w, or 0.5 to 4% w/w, or 0.5 to 3% w/w, or 0.5 to 2% w/w, or 0.5 to 1% w/w, or 0.5 to 0.9% w/w, or 0.5 to 0.8% w/w, or 0.5 to 0.7% w/w, or 0.5 to 0.6% w/w, or 0.5% w/w, or about 0.5% w/w.

Examples of linear C5 to C12 monocarboxylic acids are valeric acid (C5), caproic acid (C6), enanthic acid (C7), caprylic acid (C8), pelargonic acid (C9), capric acid (C10), undecylic acid (C11), and lauric acid (C12). In some embodiments, the linear C5 to C12 monocarboxylic acids, or salt thereof, in the compositions are caprylic acid (C8) and/or capric acid (C10), or salt thereof. Capric acid (CAS No. 334-48-5) is available commercially from Chemceed under the name of Capric Acid 99%. Caprylic acid (CAS No. 124-07-2) is available commercially from HallStar under the trade name HallStar® C-899 Caprylic Acid. In some embodiments, the linear C5 to C12 monocarboxylic acid is caprylic acid (C8). In some embodiments, the composition does not contain or is substantially free of capric acid. Blends of caprylic acid and capric acid are commercially available from Emery Oleochemicals under the trade name Emery® 658 Caprylic-Capric Acid and from Chemceed under the name of C8/C10 Fatty Acid. The commercially available blends contain approximately 60% w/w caprylic acid (C8) and approximately 40% w/w capric acid (C10) and can contain up to 0.5% w/w caproic acid (C6) and up to 1% w/w lauric acid (C12). In some embodiments, the linear C5 to C12 monocarboxylic acids in the composition are a 60:40 blend of caprylic acid to capric acid. In some embodiments, the compositions contain one or more of linear C6 monocarboxylic acid, linear C8 monocarboxylic acid, linear C10 monocarboxylic acid, or linear C12 monocarboxylic acid, or salt thereof. In some embodiments, the compositions contain one or more linear C5 to C10 monocarboxylic acids. The total concentration of the one or more linear C5 to C12 monocarboxylic acids, or salt thereof, in the compositions can be from about 0.01 to about 5% w/w. In some embodiments, the total concentration of the one or more linear C5 to C12 monocarboxylic acids, or salt thereof, in the composition is 0.01 to 5% w/w, or 0.01 to 4% w/w, or 0.01 to 3% w/w, or 0.01 to 2% w/w, or 0.01 to 1% w/w, or 0.01 to 0.9% w/w, or 0.01 to 0.8% w/w, or 0.01 to 0.7% w/w, or 0.01 to 0.6% w/w, or 0.01 to 0.5% w/w, or 0.05 to 5% w/w, or 0.05 to 4% w/w, or 0.05 to 3% w/w, or 0.05 to 2% w/w, or 0.05 to 1% w/w, or 0.05 to 0.9% w/w, or 0.05 to 0.8% w/w, or 0.05 to 0.7% w/w, or 0.05 to 0.6% w/w, or 0.05 to 0.5% w/w, or 0.1 to 5% w/w, or 0.1 to 4% w/w, or 0.1 to 3% w/w, or 0.1 to 2% w/w, or 0.1 to 1% w/w, or 0.1 to 0.9% w/w, or 0.1 to 0.8% w/w, or 0.1 to 0.7% w/w, or 0.1 to 0.6% w/w, or 0.1 to 0.5% w/w, or 0.2 to 5% w/w, or 0.2 to 4% w/w, or 0.2 to 3% w/w, or 0.2 to 2% w/w, or 0.2 to 1% w/w, or 0.2 to 0.9% w/w, or 0.2 to 0.8% w/w, or 0.2 to 0.7% w/w, or 0.2 to 0.6% w/w, or 0.2 to 0.5% w/w, or 0.3 to 5% w/w, or 0.3 to 4% w/w, or 0.3 to 3% w/w, or 0.3 to 2% w/w, or 0.3 to 1% w/w, or 0.3 to 0.9% w/w, or 0.3 to 0.8% w/w, or 0.3 to 0.7% w/w, or 0.3 to 0.6% w/w, or 0.3 to 0.5% w/w, or 0.4 to 5% w/w, or 0.4 to 4% w/w, or 0.4 to 3% w/w, or 0.4 to 2% w/w, or 0.4 to 1% w/w, or 0.4 to 0.9% w/w, or 0.4 to 0.8% w/w, or 0.4 to 0.7% w/w, or 0.4 to 0.6% w/w, or 0.4 to 0.5% w/w, or 0.5 to 5% w/w, or 0.5 to 4% w/w, or 0.5 to 3% w/w, or 0.5 to 2% w/w, or 0.5 to 1% w/w, or 0.5 to 0.9% w/w, or 0.5 to 0.8% w/w, or 0.5 to 0.7% w/w, or 0.5 to 0.6% w/w, or 0.5% w/w, or about 0.5% w/w. In some embodiments, the linear C5 to C12 monocarboxylic acid in the composition is caprylic acid (C8) at a concentration of 0.01 to 5% w/w, or 0.1 to 5% w/w, or 0.1 to 1% w/w, or 0.1 to 0.9% w/w, or 0.1 to 0.8% w/w, or 0.1 to 0.7% w/w or 0.1 to 0.6% w/w, or 0.1 to 0.5% w/w, or 0.1 to 0.4% w/w, or 0.1 to 0.3% w/w, or 0.2 to 0.9% w/w, or 0.2 to 0.8% w/w, or 0.2 to 0.7% w/w, or 0.2 to 0.6% w/w. or 0.2 to 0.5% w/w, or 0.2 to 0.4% w/w, or 0.3 to 0.9% w/w, or 0.3 to 0.8% w/w, or 0.3 to 0.7% w/w, or 0.3 to 0.6% w/w, or 0.3 to 0.5% w/w, or 0.4 to 1% w/w, or 0.4 to 0.9% w/w, or 0.4 to 0.8% w/w, or 0.4 to 0.7% w/w, or 0.4 to 0.6% w/w, or about 0.2% w/w, or about 0.5% w/w.

The compositions of the present disclosure can contain an aromatic carboxylic acid, or salt thereof, selected from benzoic acid or salt thereof and/or one or more derivatives of benzoic acid, or salt thereof. These compounds contribute to the overall antimicrobial activity of the compositions. Benzoic acid (CAS No. 65-85-0) is available commercially from Sigma-Aldrich. Derivatives of benzoic acid are compounds derived from benzoic acid and can include a similar structure to benzoic acid. Examples of derivatives of benzoic acid include aminobenzoic acids and hydroxybenzoic acids. Preferred derivatives of benzoic acid are the hydroxybenzoic acids. Examples of hydroxybenzoic acids include 3-hydroxybenzoic acid, 4-hydroxybenzoic acid and salicylic acid (2-hydroxybenzoic acid). In preferred embodiments, the aromatic carboxylic acid, or salt thereof, in the composition is salicylic acid, or salt thereof. The compounds 3-hydroxybenzoic acid (CAS No. 99-06-9) and 4-hydroxybenzoic acid (CAS No. 99-96-7) are commercially available from Sigma-Aldrich. Salicylic acid (CAS No. 69-72-7) is available commercially from Sigma Aldrich. The total concentration of the aromatic carboxylic acid, or salt thereof selected from benzoic acid or salt thereof and/or one or more derivatives of benzoic acid, or salt thereof, in the compositions can be from 0.01 to 5% w/w. In some embodiments, the total concentration of the aromatic carboxylic acid, or salt thereof, selected from benzoic acid or salt thereof and/or one or more derivatives of benzoic acid, or salt thereof, in the compositions is 0.01 to 5% w/w, or 0.01 to 4% w/w, or 0.01 to 3% w/w, or 0.01 to 2% w/w, or 0.01 to 1% w/w, or 0.01 to 0.9% w/w, or 0.01 to 0.8% w/w, or 0.01 to 0.7% w/w, or 0.01 to 0.6% w/w, or 0.01 to 0.5% w/w, or 0.01 to 0.4% w/w, or 0.01 to 0.3% w/w, or 0.01 to 0.2% w/w, or 0.05 to 5% w/w, or 0.05 to 4% w/w, or 0.05 to 3% w/w, or 0.05 to 2% w/w, or 0.05 to 1% w/w, or 0.05 to 0.9% w/w, or 0.05 to 0.8% w/w, or 0.05 to 0.7% w/w, or 0.05 to 0.6% w/w, or 0.05 to 0.5% w/w, or 0.05 to 0.4% w/w, or 0.05 to 0.3% w/w, or 0.05 to 0.2% w/w, or 0.1 to 5% w/w, or 0.1 to 4% w/w, or 0.1 to 3% w/w, or 0.1 to 2% w/w, or 0.1 to 1% w/w, or 0.1 to 0.9% w/w, or 0.1 to 0.8% w/w, or 0.1 to 0.7% w/w, or 0.1 to 0.6% w/w, or 0.1 to 0.5% w/w, or 0.1 to 0.4% w/w, or 0.1 to 0.3% w/w, or 0.1 to 0.2% w/w, or 0.2% w/w, or about 0.2% w/w, or 0.18% w/w, or about 0.18% w/w. In some embodiments, the aromatic carboxylic acid, or salt thereof, in the composition is salicylic acid, or salt thereof at a concentration of 0.01 to 5% w/w, or 0.1 to 5% w/w, or 0.1 to 0.5% w/w, or 0.1 to 0.4% w/w, or 0.1 to 0.3% w/w, or 0.1 to 0.2% w/w, or about 0.18% w/w.

In some embodiments, the one or more linear monocarboxylic acids with a carbon chain length of C5 to C12, or salt thereof is caprylic acid (C8), or salt thereof; and the derivative of benzoic acid, or salt thereof, is salicylic acid, or salt thereof. In further embodiments, the concentration of caprylic acid (C8), or salt thereof is 0.01 to 5% w/w, or 0.1 to 5% w/w, 0.1 to 1.0% w/w, or 0.1 to 0.9% w/w, or 0.1 to 0.8% w/w, or 0.1 to 0.7% w/w, or 0.1 to 0.6% w/w, or 0.1 to 0.5% w/w, or 0.1 to 0.4% w/w, or 0.1 to 0.3% w/w, or about 0.2% w/w, or about 0.5% w/w; and the concentration of salicylic acid, or salt thereof is 0.01 to 5% w/w, or 0.1 to 5% w/w, 0.1 to 1%, or 0.1 to 0.9% w/w, or 0.1 to 0.8% w/w, or 0.1 to 0.7% w/w, or 0.1 to 0.6% w/w, or 0.1 to 0.5% w/w, or 0.1 to 0.4% w/w, or 0.1 to 0.3% w/w, or 0.1 to 0.2% w/w, or about 0.18% w/w.

The compositions of the present disclosure can contain one or more C12 to C16 linear alkyl ether carboxylic acids or salt thereof. These compounds can be anionic surfactants and serve as wetting agents as well as contribute to the overall antimicrobial activity of the compositions. Non-limiting examples of these compounds include laureth-5 carboxylic acid (CAS Nos. 27306-90-7, 21127-45-7, and 220622-96-8) and sodium laureth-5 carboxylate (CAS Nos. 33939-64-9 and 38975-03-0), which are commercially available from Innospec under the tradenames Empicol® CED 5 and Empicol® CED 5S, respectively. Empicol® CED 5S is available as a 22% active aqueous liquid and contains small amounts of the preservatives methylchloroisothiazolinone and methylisothiazolinone. The desired concentration of Empicol® CED 5S in the composition can be achieved by dilution of the 22% active liquid. Laureth-5 carboxylic acid is a C12 linear alkyl ether carboxylic acid with a degree of ethoxylation of 5 moles ethylene oxide and is represented by the chemical formula: $CH_3(CH_2)_{11}(OCH_2CH_2)_nOCH_2COOH$ where n has an average value of 4. Sodium laureth-5 carboxylate is represented by the chemical formula: $CH_3(CH_2)_{11}(OCH_2CH_2)_nOCH_2COONa$ where n has an average value of 4. In some embodiments, the degree of ethoxylation in the C12 to C16 linear alkyl ether carboxylic acids or salt thereof is 5 moles of ethylene oxide. In some embodiments, the C12 to C16 linear alkyl ether ethylene oxide carboxylic acid is laureth-5 carboxylic acid. In other embodiments, the C12 to C16 linear alkyl ether carboxylic acid is the salt form sodium laureth-5 carboxylate. The total concentration of the one or more C12 to C16 linear alkyl ether carboxylic acids or salt thereof in the compositions can be from about 0.01 to about 5% w/w. In some embodiments, the total concentration of the one or more C12 to C16 linear alkyl ether carboxylic acids or salt thereof in the compositions is 0.01 to 5% w/w, or 0.01 to 4% w/w, or 0.01 to 3% w/w, or 0.01 to 2% w/w, or 0.01 to 1% w/w, or 0.01 to 0.9% w/w, or 0.01 to 0.8% w/w, or 0.01 to 0.7% w/w, or 0.01 to 0.6% w/w, or 0.01 to 0.5% w/w, or 0.01 to 0.4% w/w, or 0.01 to 0.3% w/w, or 0.01 to 0.2% w/w, or 0.01 to 0.1% w/w, or 0.01 to 0.09% w/w, or 0.01 to 0.08% w/w, or 0.01 to 0.07% w/w, or 0.01 to 0.06% w/w, or 0.01 to 0.05% w/w, or 0.02 to 5% w/w, or 0.02 to 4% w/w, or 0.02 to 3% w/w, or 0.02 to 2% w/w, or 0.02 to 1% w/w, or 0.02 to 0.9% w/w, or 0.02 to 0.8% w/w, or 0.02 to 0.7% w/w, or 0.02 to 0.6% w/w, or 0.02 to 0.5% w/w, or 0.02 to 0.4% w/w, or 0.02 to 0.3% w/w, or 0.02 to 0.2% w/w, or 0.02 to 0.1% w/w, or 0.02 to 0.09% w/w, or 0.02 to 0.08% w/w, or 0.02 to 0.07% w/w, or 0.02 to 0.06% w/w, or 0.02 to 0.05% w/w, or 0.03 to 5% w/w, or 0.03 to 4% w/w, or 0.03 to 3% w/w, or 0.03 to 2% w/w, or 0.03 to 1% w/w, or 0.03 to 0.9% w/w, or 0.03 to 0.8% w/w, or 0.03 to 0.7% w/w, or 0.03 to 0.6% w/w, or 0.03 to 0.5% w/w, or 0.03 to 0.4% w/w, or 0.03 to 0.3% w/w, or 0.03 to 0.2% w/w, or 0.03 to 0.1% w/w, or 0.03 to 0.09% w/w, or 0.03 to 0.08% w/w, or 0.03 to 0.07% w/w, or 0.03 to 0.06% w/w, or 0.03 to 0.05% w/w, or 0.04 to 5% w/w, or 0.04 to 4% w/w, or 0.04 to 3% w/w, or 0.04 to 2% w/w, or 0.04 to 1% w/w, or 0.04 to 0.9% w/w, or 0.04 to 0.8% w/w, or 0.04 to 0.7% w/w, or 0.04 to 0.6% w/w, or 0.04 to 0.5% w/w, or 0.04 to 0.4% w/w, or 0.04 to 0.3% w/w, or 0.04 to 0.2% w/w, or 0.04 to 0.1% w/w, or 0.04 to 0.09% w/w, or 0.04 to 0.08% w/w, or 0.04 to 0.07% w/w, or 0.04 to 0.06% w/w, or 0.04 to 0.05% w/w, or 0.05 to 5% w/w, or 0.05 to 4% w/w, or 0.05 to 3% w/w, or 0.05 to 2% w/w, or 0.05 to 1% w/w, or 0.05 to 0.9% w/w, or 0.05 to 0.8% w/w, or 0.05 to 0.7% w/w, or 0.05 to 0.6% w/w, or 0.05 to 0.5% w/w, or 0.05 to 0.4% w/w, or 0.05 to 0.3% w/w, or 0.05 to 0.2% w/w, or 0.05 to 0.1% w/w, or 0.05 to 0.09% w/w, or 0.05 to 0.08% w/w, or 0.05 to 0.07% w/w, or 0.05 to 0.06% w/w, or 0.05% w/w, or about 0.05% w/w, or 0.2% w/w, or about 0.2% w/w. In some embodiments, the compositions do not contain C12 to C16 linear alkyl ether carboxylic acids or salt thereof.

The compositions of the present disclosure can contain one or more sodium C8 to C16 alkyl sulfate surfactants. Sodium C8 to C16 alkyl sulfates are the salts of the sulfuric acid monoesters of fatty alcohols with a chain length varying from C8 to C16. These compounds can be anionic surfactants and can serve as wetting agents, as well as contribute to the overall antimicrobial activity of the compositions. A non-limiting example of a sodium C8 to C16 alkyl sulfate surfactants is sodium C12 alkyl sulfate which is sodium lauryl sulfate (CAS Nos. 151-21-3, 68585-47-7 (generic), 68955-19-1, 73296-89-6), also known as sodium dodecyl sulfate. Sodium lauryl sulfate (CAS No. 151-21-3) is commercially available from the Stepan Company under the trade names STEPANOL® WA-100 and STEPANOL® LCP. Another non-limiting example is a C14 alkyl sulfate known as tetradecyl sulfate sodium salt (CAS No. 1191-50-0) available from Sigma-Aldrich. Sodium C8 to C16 alkyl sulfate surfactants can contain mixtures of the sodium salts of the sulfates of fatty alcohols with different alkyl carbon chains. For example, sodium C8-C10 alkyl sulfate (commercially available under the trade name EMPICOL LB 40 available from Albright & Wilson) is the sodium salt of the sulfate of a mixture of fatty alcohols with 8 to 10 carbons in the alkyl chain, and sodium C10-C16 alkyl sulfate (commercially available under the trade name NEODOL 145B Sulfate, Sodium Salt available from Shell) is the sodium salt of the sulfate of a mixture of fatty alcohols with 10 to 16 carbons in the alkyl chain. In some embodiments, the sodium C8 to C16 alkyl sulfate surfactant in the compositions is sodium lauryl sulfate. In some embodiments, the sodium C8 to C16 alkyl sulfate surfactant in the compositions is sodium C10-C16 alkyl sulfate. In other embodiments the sodium C8 to C16 alkyl sulfate surfactant in the compositions is sodium lauryl sulfate and sodium C10-C16 alkyl sulfate. The total concentration of the one or more sodium C8 to C16 sodium alkyl sulfate surfactants in the compositions can be from about 0.01 to about 5% w/w. In some embodiments the total concentration of the one or more sodium C8 to C16 sodium alkyl sulfate surfactants in the compositions is 0.01 to 5% w/w, or 0.01 to 4% w/w, or 0.01 to 3% w/w, or 0.01 to 2% w/w, or 0.01 to 1% w/w, or 0.01 to 0.9% w/w, or 0.01 to 0.8% w/w, or 0.01 to 0.7% w/w, or 0.01 to 0.6% w/w, or 0.01 to 0.5% w/w, or 0.01 to 0.4% w/w, or 0.05 to 5% w/w, or 0.05 to 4% w/w, or 0.05 to 3% w/w, or 0.05 to 2% w/w, or 0.05 to 1% w/w, or 0.05 to 0.9% w/w, or 0.05 to 0.8% w/w, or 0.05 to 0.7% w/w, or 0.05 to 0.6% w/w, or 0.05 to 0.5% w/w, or 0.05 to 0.4% w/w, or 0.1 to 5% w/w, or 0.1 to 4% w/w, or 0.1 to 3% w/w, or 0.1 to 2% w/w, or 0.1 to 1% w/w, or 0.1 to 0.9% w/w, or 0.1 to 0.8% w/w, or 0.1 to 0.7% w/w, or 0.1 to 0.6% w/w, or 0.1 to 0.5% w/w, or 0.1 to 0.4% w/w, or 0.2 to 5% w/w, or 0.2 to 4% w/w, or 0.2 to 3% w/w, or 0.2 to 2% w/w, or 0.2 to 1% w/w, or 0.2 to 0.9% w/w, or 0.2 to 0.8% w/w, or 0.2 to 0.7% w/w, or 0.2 to 0.6% w/w, or 0.2 to 0.5% w/w, or 0.2 to 0.4% w/w, or 0.3 to 5% w/w, or 0.3 to 4% w/w, or 0.3 to 3% w/w, or 0.3 to 2% w/w, or 0.3 to 1% w/w, or 0.3 to 0.9% w/w, or 0.3 to 0.8% w/w, or 0.3 to 0.7% w/w, or 0.3 to 0.6% w/w, or 0.3 to 0.5% w/w, or 0.3 to 0.4% w/w, or 0.4 to 5% w/w, or 0.4 to 4% w/w, or 0.4 to 3% w/w, or 0.4 to 2% w/w, or 0.4 to 1% w/w, or 0.4 to 0.9% w/w, or 0.4 to 0.8% w/w, or 0.4 to 0.7% w/w, or 0.4 to 0.6% w/w, or 0.4 to 0.5% w/w, or 0.4% w/w, or about 0.4% w/w.

The compositions of the present invention can contain sodium olefin sulfonate surfactants. Sodium olefin sulfonates are mixtures of long chain sulfonate salts prepared by sulfonation of varying chain lengths of alpha olefins. For example, sodium C12-C14 olefin sulfonate is a mixture of long chain sulfonate salts prepared by sulfonation of C12-C14 alpha olefins, sodium C14-C16 olefin sulfonate is a mixture of long chain sulfonate salts prepared by sulfonation of C14-C16 alpha olefins, sodium C14-C18 olefin sulfonate is a mixture of long chain sulfonate salts prepared by sulfonation of C14-C18 alpha olefins, and sodium C16-C18 olefin sulfonate is a mixture of long chain sulfonate salts prepared by sulfonation of C16-C18 alpha olefins. Commercially available sodium olefin sulfonate surfactants are sodium C14-C16 olefin sulfonate (CAS No. 68439-57-6 available under the trade name BIO-TERGE® AS-40 available from Stepan as a 39% aqueous solution), sodium C12-C14 olefin sulfonate (available under the trade name SERDET VLC 12000 available from Elementis Specialties), and sodium C14-C18 olefin sulfonate (available under the trade name COLONIAL AOS-40 available from Colonial Chemical Inc). In some embodiments, the compositions contain sodium olefin sulfonate surfactants. In some embodiments, the compositions contain sodium (C14-C16) olefin sulfonate. In some embodiments the total concentration of the one or more sodium olefin sulfonate surfactants in the compositions is 0.01 to 5% w/w, or 0.01 to 4% w/w, or 0.01 to 3% w/w, or 0.01 to 2% w/w, or 0.01 to 1% w/w, or 0.01 to 0.9% w/w, or 0.01 to 0.8% w/w, or 0.01 to 0.7% w/w, or 0.01 to 0.6% w/w, or 0.01 to 0.5% w/w, or 0.01 to 0.4% w/w, or 0.05 to 5% w/w, or 0.05 to 4% w/w, or 0.05 to 3% w/w, or 0.05 to 2% w/w, or 0.05 to 1% w/w, or 0.05 to 0.9% w/w, or 0.05 to 0.8% w/w, or 0.05 to 0.7% w/w, or 0.05 to 0.6% w/w, or 0.05 to 0.5% w/w, or 0.05 to 0.4% w/w, or 0.1 to 5% w/w, or 0.1 to 4% w/w, or 0.1 to 3% w/w, or 0.1 to 2% w/w, or 0.1 to 1% w/w, or 0.1 to 0.9% w/w, or 0.1 to 0.8% w/w, or 0.1 to 0.7% w/w, or 0.1 to 0.6% w/w, or 0.1 to 0.5% w/w, or 0.1 to 0.4% w/w, or 0.2 to 5% w/w, or 0.2 to 4% w/w, or 0.2 to 3% w/w, or 0.2 to 2% w/w, or 0.2 to 1% w/w, or 0.2 to 0.9% w/w, or 0.2 to 0.8% w/w, or 0.2 to 0.7% w/w, or 0.2 to 0.6% w/w, or 0.2 to 0.5% w/w, or 0.2 to 0.4% w/w, or 0.3 to 5% w/w, or 0.3 to 4% w/w, or 0.3 to 3% w/w, or 0.3 to 2% w/w, or 0.3 to 1% w/w, or 0.3 to 0.9% w/w, or 0.3 to 0.8% w/w, or 0.3 to 0.7% w/w, or 0.3 to 0.6% w/w, or 0.3 to 0.5% w/w, or 0.3 to 0.4% w/w, or 0.4 to 5% w/w, or 0.4 to 4% w/w, or 0.4 to 3% w/w, or 0.4 to 2% w/w, or 0.4 to 1% w/w, or 0.4 to 0.9% w/w, or 0.4 to 0.8% w/w, or 0.4 to 0.7% w/w, or 0.4 to 0.6% w/w, or 0.4 to 0.5% w/w, or 0.4% w/w, or about 0.4% w/w.

The compositions of the present invention can contain alkyl ether sulfate surfactants. Alkyl ether sulfates are the salts of sulfuric acid monoesters of alkoxylated alcohols. Non-limiting examples of alkyl ether sulfate surfactants include sodium laureth sulfate and sodium trideceth sulfate. Sodium trideceth sulfate (CAS No. 25446-78-0) is commercially available under the trade name CEDEPAL® TD-407 available from Stepan. Sodium laureth sulfate (CAS No. 68585-34-2) is commercially available under the trade name STEOL® CS-130 available from Stepan. In some embodiments, the compositions contain alkyl ether sulfate surfactants. In some embodiments, the compositions contain sodium trideceth sulfate. In some embodiments the total concentration of the alkyl ether sulfate surfactants in the compositions is 0.01 to 5% w/w, or 0.01 to 4% w/w, or 0.01 to 3% w/w, or 0.01 to 2% w/w, or 0.01 to 1% w/w, or 0.01 to 0.9% w/w, or 0.01 to 0.8% w/w, or 0.01 to 0.7% w/w, or 0.01 to 0.6% w/w, or 0.01 to 0.5% w/w, or 0.01 to 0.4% w/w, or 0.05 to 5% w/w, or 0.05 to 4% w/w, or 0.05 to 3% w/w, or 0.05 to 2% w/w, or 0.05 to 1% w/w, or 0.05 to 0.9% w/w, or 0.05 to 0.8% w/w, or 0.05 to 0.7% w/w, or 0.05 to 0.6% w/w, or 0.05 to 0.5% w/w, or 0.05 to 0.4% w/w, or 0.1 to 5% w/w, or 0.1 to 4% w/w, or 0.1 to 3% w/w, or 0.1 to 2% w/w, or 0.1 to 1% w/w, or 0.1 to 0.9% w/w, or 0.1 to 0.8% w/w, or 0.1 to 0.7% w/w, or 0.1 to 0.6% w/w, or 0.1 to 0.5% w/w, or 0.1 to 0.4% w/w, or 0.2 to 5% w/w, or 0.2 to 4% w/w, or 0.2 to 3% w/w, or 0.2 to 2% w/w, or 0.2 to 1% w/w, or 0.2 to 0.9% w/w, or 0.2 to 0.8% w/w, or 0.2 to 0.7% w/w, or 0.2 to 0.6% w/w, or 0.2 to 0.5% w/w, or 0.2 to 0.4% w/w, or 0.3 to 5% w/w, or 0.3 to 4% w/w, or 0.3 to 3% w/w, or 0.3 to 2% w/w, or 0.3 to 1% w/w, or 0.3 to 0.9% w/w, or 0.3 to 0.8% w/w, or 0.3 to 0.7% w/w, or 0.3 to 0.6% w/w, or 0.3 to 0.5% w/w, or 0.3 to 0.4% w/w, or 0.4 to 5% w/w, or 0.4 to 4% w/w, or 0.4 to 3% w/w, or 0.4 to 2% w/w, or 0.4 to 1% w/w, or 0.4 to 0.9% w/w, or 0.4 to 0.8% w/w, or 0.4 to 0.7% w/w, or 0.4 to 0.6% w/w, or 0.4 to 0.5% w/w, or 0.4% w/w, or about 0.4% w/w.

In some embodiments the compositions of the present disclosure do not contain or are substantially free of additional anionic surfactants, other than C12 to C16 linear alkyl ether carboxylic acids, or salt thereof, sodium C8 to C16 alkyl sulfate surfactants, sodium olefin sulfonate surfactants, and/or alkyl ether sulfate surfactants. In some embodiments the compositions of the present disclosure do not contain or are substantially free of anionic surfactants other than laureth-5 carboxylic acid, sodium lauryl sulfate, sodium C14-C16 olefin sulfonate, and/or sodium trideceth sulfate. In some embodiments the compositions of the present disclosure do not contain or are substantially free of anionic surfactants other than sodium laureth-5 carboxylate, sodium lauryl sulfate, sodium C14-C16 olefin sulfonate, and/or sodium trideceth sulfate. In some embodiments, the compositions of the present disclosure do not contain or are substantially free of any additional surfactant other than sodium olefin sulfonate surfactants. In some embodiments, the compositions of the present disclosure do not contain or are substantially free of any additional surfactant other that sodium C14-C16 olefin sulfonate. In some embodiments, the compositions of the present disclosure do not contain or are substantially free of sodium olefin sulfonates and/or alkyl ether sulfate surfactants. In some embodiments, the compositions do not contain or are substantially free of non-ionic surfactants, cationic surfactants, or amphoteric surfactants. The compositions of the present disclosure can contain additional surfactants. As used herein and for the purposes of the present disclosure, the term "surfactant" or "surface active agent" means a compound or material or substance that exhibits the ability to lower the surface tension of water or to reduce the interfacial tension between two immiscible substances and includes anionic, cationic, nonionic, amphoteric, and/or phospholipid surfactants. Non-limiting examples of surfactants can be found in McCutcheon's Emulsifiers & Detergents, North American Edition, Vol. 1 (2001) pages 1-227 herein incorporated by reference, and also in the International Cosmetic Ingredient Dictionary and Handbook (INCI), 12th Edition, 2008, herein incorporated by reference. Such examples include, but are not limited to, the following: block polymers, e.g., poloxamer 124 and other poloxamers; ethoxylated alcohols e.g., ceteth-2, ceteareth-20, laureth-3; ethoxylated fatty esters and oils, e.g., PEG-40 hydrogenated castor oil, PEG-36 castor oil, PEG-150 distearate; glycerol esters, e.g., polyglyceryl-3 diisostearate, glyceryl stearate; glycol esters, PEG-12 dioleate, LEXEMUL P; phosphate esters, e.g., cetyl phosphate; polymeric surfactants, e.g., PVM/MA copolymer, PVM/MA copolymer, acrylates/C10-30 alkyl acrylate crosspolymer; quaternary surfactants, e.g., cetrimonium chloride; silicone based surfactants, e.g., PEG/PPG-20/6 dimethicone; sorbitan derivatives, e.g., sorbitan stearate, polysorbate 80; sucrose and glucose esters and derivatives, e.g., PEG-20 methyl glucose sesquistearate; and sulfates of alcohols, e.g., sodium lauryl sulfate. More generally, surfactants can be classified by their ionic type such as anionic, cationic, nonionic, zwitterionic, or amphoteric. They can also be classified by their chemical structures, such as amine oxides, block polymers and block copolymers, betaines, ethoxylated alcohols, ethoxylated fatty esters and oils, glycerol esters, glycol esters, phosphate esters, polymeric surfactants, sarcosinate surfactants, quaternary surfactants, quaternary ammonium surfactants, silicone-based surfactants, sorbitan derivatives, sucrose and glucose esters and derivatives, and sulfates of alcohols. Other non-limiting examples of surfactants include anionic surfactants such as C8-C16 alkyl aryl sulfonic acids and salt thereof, C6-C22 alkyl diphenyl oxide sulfonic acids and salt thereof, C8-C22 alkyl sulfonic acids and salt thereof, sulfonated C12 to C22 carboxylic acids and salt thereof, alkyl or alkenyl esters or diesters of sulfosuccinic acid and salt thereof, naphthalene sulfonic acids and salt thereof, alkyl polyglucoside surfactants, anionic sulfonic acid based surfactants and their salt, nonionic ethoxylated alcohols, C12-C14 fatty acid monoalkanol amides, polyoxyethylene alkyl ether phosphates, alkyl sulfates, sodium C8 to C16 alkyl sulfates, sodium C10 to C16 alkyl sulfates, sodium lauryl sulfate, sodium olefin sulfonates, sodium (C6-C24) olefin sulfonate, sodium (C14-C16) olefin sulfonate, alkyl ether sulfates, sodium ether sulfates, ammonium ether sulfates, sodium trideceth sulfate, sodium laureth sulfate, and C6 to C10 linear alkyl ether carboxylic acids and salt thereof. In some embodiments, the compositions do not contain or are substantially free of cationic, nonionic, amphoteric, zwitterionic, and/or phospholipid surfactants. In some embodiments, the compositions do not contain or are substantially free of amine oxide surfactants, betaine surfactants, block polymers, block copolymers, reverse triblock copolymers, poloxamers, quaternary surfactants, quaternary ammonium surfactants, and/or sarcosinate surfactants. In some embodiments, the compositions do not contain or are substantially free of C8-C16 alkyl aryl sulfonic acids and salt thereof, C6-C22 alkyl diphenyl oxide sulfonic acids and salt thereof, C8-C22 alkyl sulfonic acids and salt thereof, sulfonated C12 to C22 carboxylic acids and salt thereof, alkyl or alkenyl esters or diesters of sulfosuccinic acid and salt thereof, naphthalene sulfonic acids and salt thereof, alkyl polyglucoside surfactants, anionic sulfonic acid based surfactants and their salt, nonionic ethoxylated alcohols, C12-C14 fatty acid monoalkanol amides, polyoxyethylene alkyl ether phosphates, and/or C6 to C10 linear alkyl ether carboxylic acids and salt thereof. In some embodiments, the compositions of the present disclosure do not contain or are substantially free of aryl sulfonic acids or salts thereof. Non-limiting examples of aryl sulfonic acids include xylene sulfonic acid, cumene sulfonic acid, toluene sulfonic acid, polyether phosphate esters, and diphenyloxide disulfonates. In some embodiments, the compositions of the present disclosure do not contain or are substantially free of aryl sulfonates. Non-limiting examples of aryl sulfonates include sodium xylene sulfonate, sodium cumene sulfonate, sodium toluene sulfonate. In some embodiments, the compositions of the present disclosure do not contain or are substantially free of non-surfactant sulfonic acids or salts thereof. Non-limiting examples of non-surfactant sulfonic acids include benzenesulfonic acid, benzene di sulfonic acid, xylene sulfonic acid, toluene sulfonic acid, cumene sulfonic acid, sulfosalicylic acid, naphthalene mono- or di-sulfonic acid, methane sulfonic acid, sulfosuccinic acid, and isethionic acid. In some embodiments, the composition of the present disclosure does not contain or is substantially free of a fluorescent active compound, non-limiting examples of which are alkyl aryl sulfonates, sodium xylene sulfonate, xylene sulfonate, sodium cumene sulfonate, cumene sulfonate, toluene sulfonate, sodium toluene sulfonate, benzene sulfonate, alkyl diphenyl oxide disulfonate, sodium alkyl diphenyl disulfonate, sodium naphthalene sulfonate, naphthalene sulfonate, naphthalene disulfonate, disodium naphthalene disulfonate, and alkyl naphthalene sulfonate.

In some embodiments, the compositions of the present disclosure do not contain or are substantially free of additional carboxylic acids other than one or more linear monocarboxylic acids with a carbon chain length of C1 to C4 or salt thereof, and one or more linear monocarboxylic acids with a carbon chain length of C5 to C12 or salt thereof, and one or more aromatic carboxylic acids and salt thereof selected from benzoic acid and/or derivatives of benzoic acid or salt thereof. In some embodiments, the compositions do not contain or are substantially free of additional carboxylic acids other than one or more linear monocarboxylic acids with a carbon chain length of C1 to C4 or salt thereof, and one or more linear monocarboxylic acids with a carbon chain length of C5 to C12 or salt thereof, and benzoic acid and/or one or more derivatives of benzoic acid or salt thereof. In some embodiments, the compositions do not contain or are substantially free of additional carboxylic acids other than one or more linear monocarboxylic acids with a carbon chain length of C1 to C4 or salt thereof, and one or more linear monocarboxylic acids with a carbon chain length of C5 to C12 or salt thereof, and salicylic acid or salt thereof. In some embodiments, the compositions do not contain or are substantially free of additional carboxylic acids other than formic acid or salt thereof, and one or more linear monocarboxylic acids with a carbon chain length of C5 to C12 or salt thereof, and salicylic acid or salt thereof. In some embodiments, the compositions do not contain or are substantially free of additional carboxylic acids other than formic acid or salt thereof, caprylic acid and/or capric acid or salt thereof, and salicylic acid or salt thereof. In some embodiments, the compositions do not contain or are substantially free of 2-furoic acid (2-furan carboxylic acid) or salt thereof, and/or sulfoperoxycarboxylic acids or salt thereof. In some embodiments, the compositions do not contain or are substantially free of acetic acid or salt thereof. In some embodiments, the compositions do not contain or are substantially free of peracids, organic peracids, inorganic peracids, peroxyacids, percarboxylic acids, and/or peroxycarboxylic acids. In some embodiments, the compositions do not contain or are substantially free of peracetic acid (peroxyacetic acid) and/or performic acid.

The compositions of the present disclosure can optionally further include additional antimicrobial agents. Non-limiting examples of antimicrobial agents can be found in McCutcheon's Functional Materials North American Edition Vol. 2 (2001), pages 2-10 and McCutcheon's Functional Materials International Edition Vol. 2 (2001), pages 2-6, both of which are herein incorporated by reference. Other examples of suitable antimicrobial agents include phenoxyethanol and phenethyl alcohol (phenylethyl alcohol). Phenoxyethanol CAS No. 122-99-6 is an aromatic C8 alcohol. Phenethyl alcohol (also known as phenylethyl alcohol, 2-phenylethanol, PEA, benzyl carbinol) CAS No. 60-12-8, is an aromatic C8 alcohol with a characteristic mild rose-like odor. Phenethyl alcohol is known as a fragrance component having some antimicrobial properties. Phenethyl alcohol or phenoxyethanol can be at a concentration in the composition of from 0.01 to 5% w/w, or from 0.01 to 4% w/w, or from 0.01 to 3% w/w, or from 0.01 to 2% w/w, or from 0.01 to 1% w/w, or from 0.01 to less than 1% w/w, or from 0.01 to 0.9% w/w, or from 0.01 to 0.8% w/w, or from 0.1 to 5% w/w, or from 0.1 to 4% w/w, or from 0.1 to 3% w/w, or from 0.1 to 2% w/w, or from 0.1 to 1% w/w, or from 0.1 to less than 1% w/w, or from 0.1 to 0.9% w/w, or from 0.1 to 0.8% w/w. In some embodiments, the composition of the invention further comprises phenethyl alcohol. In some embodiment, the composition of the invention further comprises phenoxyethanol. In some embodiments, the compositions of the present disclosure do not contain additional antimicrobial agents other than an oxidizing agent. In some embodiments, the compositions do not contain additional antimicrobial agents other than hydrogen peroxide. In other embodiments, the compositions contain additional antimicrobials. In some embodiments, the compositions of the present disclosure contain additional antimicrobial agents that are preservatives present in the raw material components of the compositions, generally at trace amounts. In some embodiments, the compositions contain phenoxyethanol and/or phenethyl alcohol (phenylethyl alcohol). In other embodiments, the compositions do not contain or are substantially free of phenoxyethanol and/or phenethyl alcohol (phenylethyl alcohol). In some embodiments, the compositions contain methylchloroisothiazolinone and/or methylisothiazolinone. In some embodiments, the compositions contain methylchloroisothiazolinone and/or methylisothiazolinone at a total concentration of about 0.00002% w/w to about 0.02% w/w.

The compositions of the present disclosure can optionally further include a sequestering or chelating agent. The sequestering agent or chelating agent can provide stability to the hydrogen peroxide in the compositions by binding metal ions which may be detrimental to the stability of the peroxide. The sequestering or chelating agent can be phosphorus-based. A non-limiting example of a phosphorus-based sequestering or chelating agent is etidronic acid, or salt thereof, also known as hydroxyethylidene diphosphonic acid or 1-hydroxyethylidene-1,1-diphosphonic acid (HEDP). Etidronic acid (CAS No. 2809-21-4) is commercially available in a 60% active aqueous solution available from Sigma-Aldrich and also from Compass Chemical International LLC under the trade name MAYOQUEST 1500. In some embodiments, the sequestering or chelating agent in the compositions is etidronic acid (HEDP), or salt thereof. Non-limiting examples of sequestering agents or chelating agents include ethylenediaminetetraacetic acid (EDTA), diethylenetriaminepentaacetic acid (DTPA), N-(hydroxyethyl)ethylenediaminetriacetic acid (HEDTA), nitrilotriacetic acid (NTA), 2-hydroxyethyliminodiacetic acid (HEIDA) all of which are available commercially. Other non-limiting examples of sequestering agents or chelating agents can be found in McCutcheon's Functional Materials North American Edition Vol. 2 (2001), pages 31-37 and McCutcheon's Functional Materials International Edition Vol. 2 (2001), pages 16-19, both of which are herein incorporated by reference. The amount of the sequestering or chelating agent can be at a concentration which maintains an acceptable shelf-life stability of the hydrogen peroxide concentration in the composition, e.g. 1 or more years. The concentration of the sequestering or chelating agent in the compositions can be from about 0.01 to about 5% w/w. In some embodiments, the sequestering or chelating agent is 0.01 to 5% w/w, or 0.01 to 4% w/w, or 0.01 to 3% w/w, or 0.01 to 2% w/w, or 0.01 to 1% w/w, or 0.01 to 0.9% w/w, or 0.01 to 0.8% w/w, or 0.01 to 0.7% w/w, or 0.01 to 0.6% w/w, or 0.01 to 0.5% w/w, or 0.01 to 0.4% w/w, or 0.01 to 0.3% w/w, or 0.05 to 5% w/w, or 0.05 to 4% w/w, or 0.05 to 3% w/w, or 0.05 to 2% w/w, or 0.05 to 1% w/w, or 0.05 to 0.9% w/w, or 0.05 to 0.8% w/w, or 0.05 to 0.7% w/w, or 0.05 to 0.6% w/w, or 0.05 to 0.5% w/w, or 0.05 to 0.4% w/w, or 0.05 to 0.3% w/w, or 0.1 to 5% w/w, or 0.1 to 4% w/w, or 0.1 to 3% w/w, or 0.1 to 2% w/w, or 0.1 to 1% w/w, or 0.1 to 0.9% w/w, or 0.1 to 0.8% w/w, or 0.1 to 0.7% w/w, or 0.1 to 0.6% w/w, or 0.1 to 0.5% w/w, or 0.1 to 0.4% w/w, or 0.1 to 0.3% w/w, or 0.2 to 5% w/w, or 0.2 to 4% w/w, or 0.2 to 3% w/w, or 0.2 to 2% w/w, or 0.2 to 1% w/w, or 0.2 to 0.9% w/w, or 0.2 to 0.8% w/w, or 0.2 to 0.7% w/w, or 0.2 to 0.6% w/w, or 0.2 to 0.5% w/w, or 0.2 to 0.4% w/w, or 0.2 to 0.3% w/w, or 0.3 to 5% w/w, or 0.3 to 4% w/w, or 0.3 to 3% w/w, or 0.3 to 2% w/w, or 0.3 to 1% w/w, or 0.3 to 0.9% w/w, or 0.3 to 0.8% w/w, or 0.3 to 0.7% w/w, or 0.3 to 0.6% w/w, or 0.3 to 0.5% w/w, or 0.3 to 0.4% w/w, or 0.3% w/w, or about 0.3% w/w.

The compositions of the present disclosure can be acidic and can have a pH of about 0.1 to less than 7, or about 0.1 to about 6, or about 0.1 to about 5, or about 0.1 to about 4, or about 0.1 to about 3, or about 0.1 to about 2, or about 0.5 to less than 7, or about 0.5 to about 6, or about 0.5 to about 5, or about 0.5 to about 4, or about 0.5 to about 3, or about 0.5 to about 2, or about 1 to less than 7, or about 1 to about 6, or about 1 to about 5, or about 1 to about 4, or about 1 to about 3, or about 1 to about 2, or about 2. The acid pH of the compositions can be obtained by the addition of pH adjusters and buffers know in the art. Non-limiting examples pH adjusters include hydrochloric acid, citric acid and/or salt thereof, and phosphoric acid and/or salt thereof. The acidic pH of the compositions can also be obtained with the carboxylic acids present in the compositions without the need for additional pH adjusters.

The compositions of the present disclosure can further contain rheology modifiers. Non-limiting examples of rheology modifiers include sodium polyacrylate, carbomer, natural gum, natural gum derivatives, clay, modified clay, cellulose, cellulose derivative, magnesium aluminum silicate, gellan gum, xanthan gum, starch, and modified starch and cellulose ethers. Non-limiting examples of alkyl cellulose ethers include methyl cellulose (MC), ethyl cellulose (EC), and ethyl methyl cellulose (EMC). Non-limiting examples of hydroxyalkyl cellulose ethers include hydroxyethyl cellulose (HEC), hydroxylpropyl cellulose (HPC), hydroxymethyl cellulose (HMC), hydroxypropylmethyl cellulose (HPMC), ethylhydroxyethyl cellulose (EHEC), hydroxyethylmethy cellulose (HEMC), methylhydroxyethyl cellulose (MHEC), methylhydroxypropylcellulose (MHPC), and hydroxyethylcarboxymethyl cellulose (HECMC). Non-limiting examples of a carboxyalkyl cellulose ethers include carboxymethyl cellulose (CMC) and carboxymethylhydroxyethylcellulose (CMHEC).

The compositions of the present disclosure can further contain other components such as dyes, fragrances, corrosion inhibitors, and peroxide stabilizers. Generally, these components do not contribute to the overall antimicrobial activity of the compositions and generally can be at concentrations from 0.00001% w/w to 5% w/w. Phenethyl alcohol (C8) can be used as a fragrance component having some antimicrobial properties and is suitable for use in the compositions of the invention. A suitable fragrance can be wintergreen oil. The amount of fragrance in the composition can vary depending on preference, but generally can be from 0.01 to 0.5% w/w. In some embodiments, the compositions do not contain or are substantially free of quaternary ammonium compounds, humectants, zinc compounds, triazole corrosion inhibitors, benzotriazole, a methyl substituted triazole derivative, and/or lauric arginate ethyl ester.

The compositions of the present disclosure can be aqueous-based formulations. As used herein, the terms "aqueous" or "aqueous-based" with respect to a composition means a composition with water being the component with the greatest concentration level in the composition. In some embodiments, the composition can comprise greater than 50% w/w, at least 60% w/w, at least 70% w/w, at least 80% w/w, at least 90% w/w, at least 91% w/w, at least 92% w/w, at least 93% w/w, at least 94% w/w, at least 95% w/w, at least 96% w/w, at least 97% w/w, at least 98% w/w, or at least 99% w/w, or any range therein, of water. In some preferred embodiments, the composition can comprise at least 90% w/w, more preferably at least 95% w/w, or even more preferably at least 97% w/w water. In other embodiments, the composition can comprise 95 to 99% w/w, or 95 to 98.5% w/w, or 95 to 98% w/w, or 96 to 99% w/w, or 96 to 98.5% w/w, or 96 to 98% w/w, or 97 to 99% w/w water, or 97 to 98.5% w/w, or 97 to 98% w/w. The concentration of water in the composition can also be determined by the formula: 100% minus the collective concentrations of the other ingredients in the composition (on a dry basis). Alternatively, the concentration of water in the composition can be represented by the term "q.s. to 100%", which means a sufficient quantity of water to make 100% w/w of the total composition. The water can preferably be purified, distilled, or deionized (DI) water.

The compositions can be formulated as liquid solutions, thickened solutions, or gels. The compositions can be stored in suitable containers compatible with hydrogen peroxide and the other components. Non-limiting examples include plastic or stainless steel containers. The compositions can be packaged in containers suitable for commercial distribution and sale, non-limiting examples of which include bottles, jars, tubs, buckets, barrels, spray bottles, and aerosol containers. The compositions can be incorporated into wipes or cloths compatible with hydrogen peroxide and packaged as pre-moistened wipes in pouches, sachets, jars, or tubs.

The compositions of the present disclosure can be formulated as concentrates, i.e. formulas with lower amounts of water, which can be reconstituted with water prior to use to obtain concentrations of the hydrogen peroxide and other components to the levels of the full strength compositions as disclosed in this disclosure.

Manufacture

The compositions of the present disclosure can be manufactured by methods and equipment known in the art for the manufacture of liquid products such as surface cleaners and disinfectants. Such methods include, but are not limited to the use of mechanical mixers, dissolvers, dispersers, homogenizers, and mills. Non-limiting examples include LIGHTNIN propeller mixers, COWLES dissolvers, IKA ULTRA TURRAX dispersers, and SILVERSON homogenizers. The compositions can be made in vessels made of materials such as stainless steel that do not react with the compositions or any of the components. The compositions of the disclosure can be manufactured from small laboratory scale batches using laboratory mixing equipment to full-scale production batches.

Antimicrobial and Microbicidal Activity of the Compositions

Antimicrobial effectiveness testing data has demonstrated that the compositions of the present disclosure have exhibited broad spectrum antimicrobial and microbicidal activity against a variety of organisms including bacteria (including gram positive bacteria, gram negative bacteria, and mycobacteria), and fungi (including yeasts and molds). Non-limiting examples of microorganisms include bacteria, including gram-positive bacteria, gram-negative bacteria, and mycobacteria; fungi, including yeasts and molds; viruses; and spores. An example of a gram-positive bacteria is *Staphylococcus aureus*. Examples of gram-negative bacteria include *Pseudomonas aeruginosa* and *Escherichia coli*. An example of mycobacteria is *Mycobacterium avium*. An example of a yeast is *Candida albicans*. An example of a mold is *Aspergillus brasiliensis*.

In some embodiments, the compositions of the present disclosure are antibacterial, antifungal, antiviral, and/or antimycobacterial. In some embodiments, the compositions are bactericidal, fungicidal, viricidal, mycobactericidal, and/or sporicidal.

In some embodiments, the antimicrobial and microbicidal activity of the compositions of the present disclosure is due to the presence of hydrogen peroxide in combination with one or more of the following individual components: one or more linear monocarboxylic acids with a carbon chain length of C1 to C4, or salt thereof; one or more linear monocarboxylic acids with a carbon chain length of C5 to C12, or salt thereof; an aromatic carboxylic acid, or salt thereof, selected from benzoic acid and/or one or more derivatives of benzoic acid, or salt thereof; one or more C12 to C16 linear alkyl ether carboxylic acids, or salt thereof; one or more sodium C8 to C16 alkyl sulfate surfactants; or one or more sodium olefin sulfonate surfactants. In some embodiments, the antimicrobial and microbicidal activity of the compositions of the present disclosure is due to the presence of hydrogen peroxide in combination with the following group of components as a whole: one or more linear monocarboxylic acids with a carbon chain length of C1 to C4, or salt thereof; one or more linear monocarboxylic acids with a carbon chain length of C5 to C12, or salt thereof; an aromatic carboxylic acid, or salt thereof, selected from benzoic acid and/or one or more derivatives of benzoic acid, or salt thereof; and a surfactant selected from one or more C12 to C16 linear alkyl ether carboxylic acids, or salt thereof; one or more sodium C8 to C16 alkyl sulfate surfactants; or one or more sodium olefin sulfonate surfactants.

In some embodiments, the antimicrobial and microbicidal activity of the compositions of the present disclosure is due to the synergism of hydrogen peroxide with one or more of the following individual components: one or more linear monocarboxylic acids with a carbon chain length of C1 to C4, or salt thereof; one or more linear monocarboxylic acids with a carbon chain length of C5 to C12, or salt thereof; an aromatic carboxylic acid, or salt thereof, selected from benzoic acid and/or one or more derivatives of benzoic acid, or salt thereof; one or more C12 to C16 linear alkyl ether carboxylic acids, or salt thereof; one or more sodium C8 to C16 alkyl sulfate surfactants; or one or more sodium olefin sulfonate surfactants. In some embodiments, the antimicrobial and microbicidal activity of the compositions of the present disclosure is due to the synergism of hydrogen peroxide with the following group of components as a whole: one or more linear monocarboxylic acids with a carbon chain length of C1 to C4, or salt thereof; one or more linear monocarboxylic acids with a carbon chain length of C5 to C12, or salt thereof; an aromatic carboxylic acid, or salt thereof, selected from benzoic acid and/or one or more derivatives of benzoic acid, or salt thereof; and a surfactant selected from one or more C12 to C16 linear alkyl ether carboxylic acids, or salt thereof; one or more sodium C8 to C16 alkyl sulfate surfactants; or one or more sodium olefin sulfonate surfactants.

In some embodiments, the antimicrobial and microbicidal activity of the compositions of the present disclosure is due to the synergism of hydrogen peroxide with one or more of the following individual components: one or more linear monocarboxylic acids with a carbon chain length of C1 to C4, or salt thereof; caprylic acid or salt thereof, and/or capric acid or salt thereof; salicylic acid, or salt thereof; laureth-5 carboxylic acid or sodium laureth-5 carboxylate; sodium lauryl sulfate; or sodium C14-C16 olefin sulfonate. In some embodiments, the antimicrobial and microbicidal activity of the compositions of the present disclosure is due to the synergism of hydrogen peroxide with the following group of components as a whole: one or more linear monocarboxylic acids with a carbon chain length of C1 to C4, or salt thereof; caprylic acid or salt thereof, and/or capric acid or salt thereof; salicylic acid, or salt thereof; and a surfactant selected from laureth-5 carboxylic acid or sodium laureth-5 carboxylate, sodium lauryl sulfate, or sodium C14-C16 olefin sulfonate.

Surprisingly, a synergistic antimicrobial and microbicidal effect against mycobacteria was demonstrated between caprylic acid and salicylic acid. An example of this synergism is illustrated in one aspect of the present invention in the results of Example 3 below. The effect was not seen between capric acid and salicylic acid.

Methods of Use

The disinfectant compositions disclosed in the present disclosure can be useful for the disinfection or sterilization of a variety of surfaces and have exhibited broad spectrum antimicrobial activity and/or microbicidal activity against a variety of microorganisms on surfaces. Disclosed herein are methods of disinfecting or sterilizing a surface, the methods comprising: contacting the compositions of the present disclosure with the surface and allowing the composition to remain in contact with the surface for a period of time, thereby disinfecting or sterilizing the surface. Non-limiting examples of microorganisms include bacteria, including gram-positive bacteria, gram-negative bacteria, and mycobacteria; fungi, including yeasts and molds; viruses; and spores.

Prior to use, the surfaces should be clean and free from debris. The compositions can be used full strength without dilution by applying the composition onto a surface, waiting for a period of time (contact time), e.g. at least 1 minute, and then removing the composition (e.g., by rinsing with water or wiping with a clean paper towel or cloth) or allowing it to dry without removal. The compositions can be applied by pouring or spraying directly onto the surface, or can be applied to a clean paper towel or cloth and then applied to the surface. The compositions can be applied to a surface from a pre-moistened wipe by spreading the composition over the surface with the wipe. In some embodiments, the contact time is about 30 seconds, or about 1 minute, or about 1 and a half minutes (90 seconds), or about 2 minutes, or about 3 minutes, or about 4 minutes, or about 5 minutes, or about 10 minutes, or any range therein. In some embodiments, the contact time is least about 30 seconds, or at least about 45 seconds, or at least about 1 minute, or at least about 1.5 minutes, or at least about 2 minutes, or at least about 3 minutes, or at least about 4 minutes, or at least about 5 minutes, or at least about 10 minutes. In some embodiments, the contact time is greater than 5 minutes. In certain embodiments, the contact time is about 30 seconds to about 10 minutes, or about 45 second to about 5 minutes, or about 30 seconds to about 1 minute, or about 30 seconds to about 90 seconds, or about 30 seconds to about 2 minutes, or about 30 seconds to about 3 minutes, or about 30 seconds to about 4 minutes, or about 30 seconds to about 5 minutes, or about 30 seconds to about 10 minutes, or about 1 minute to about 90 seconds, or about 1 minute to about 2 minutes, or about 1 minute to about 3 minutes, or about 1 minute to about 4 minutes, or about 1 minute to about 5 minutes, or about 1 minute to about 10 minutes.

The compositions can be useful for the disinfection or sterilization of hard surfaces (i.e., non-porous), for example, environmental surfaces found in dental, hospital, medical, clinical, and food handling/preparation environments. Non-limiting examples of hard surfaces include: counters; furniture; walls; floors; medical (e.g., dental, clinical, or hospital) equipment, devices, tools, and instruments; food preparation and handling equipment, appliances, and utensils; and bathroom fixtures. It is contemplated that the compositions of the present disclosure can be used for disinfection or sterilization of skin and other biological surfaces. In some embodiments, the compositions are not used to disinfect a space.

EXAMPLES

The following examples are included to demonstrate certain non-limiting aspects of the disclosure. It should be appreciated by those of skill in the art that the techniques disclosed in the examples that follow represent techniques discovered by the inventors to function well in the practice of the disclosure. However, those of skill in the art should, in light of the present disclosure, appreciate that many changes can be made in the specific embodiments that are disclosed and still obtain a like or similar result without departing from the spirit and scope of the disclosure.

Example 1—Hydrogen Peroxide Disinfectant Formulas

The disinfectant formulas listed in Table 1 were made according to the following procedure: The Etidronic Acid (HEDP) was added to the water and mixed until dissolved. Next, the hydrogen peroxide was added and mixed until dissolved. Then, the remaining ingredients were added in no particular order and mixed until dissolved. The formulas were translucent liquids. The formulas listed in Table 1 are full-strength formulas ready for use. The pH values of the formulas are also reported in Table 1.

TABLE 1

| | | Formula ID & % w/w of total composition | | | | | |
|---|---|---|---|---|---|---|---|
| Ingredient | CAS No. | A | B | C | D | E | F |
| Hydrogen Peroxide[1] | 7722-84-1 | 0.5 | 0.5 | 0.5 | 0.5 | 0.5 | 0.5 |
| Etidronic Acid (HEDP)[2] | 2809-21-4 | 0.3 | 0.3 | 0.3 | 0.3 | 0.3 | 0.3 |
| Formic Acid | 64-18-6 | 0.5 | 0.5 | 0.5 | 0.5 | 0.5 | 0.5 |
| Sodium Laureth-5 Carboxylate[3,4] | 33939-64-9 | — | 0.2 | 0.05 | 0.05 | 0.05 | 0.05 |
| Sodium Lauryl Sulfate | 151-21-3 | — | — | 0.4 | 0.4 | 0.4 | 0.4 |
| Caprylic Acid[5] | 124-07-2 | — | — | — | 0.3 | — | 0.3 |
| Capric Acid5 | 334-48-5 | — | — | — | 0.2 | — | 0.2 |
| Salicylic Acid | 69-72-7 | — | — | — | — | 0.18 | 0.18 |
| DI Water | — | q.s. to 100% | q.s. to 100% | q.s. to 100% | q.s. to 100% | q.s. to 100% | q.s. to 100% |
| pH Readings | | 1.85 | 1.97 | 1.96 | 1.40 | 1.81 | 1.32 |

[1]Added 1.43% w/w of a 35% active solution to give 0.5% w/w of Hydrogen Peroxide
[2]Added 0.5% w/w of a 60% active solution to give 0.3% w/w of Etidronic Acid (HEDP)
[3]Added 0.91% w/w of a 22% active solution to give 0.2% w/w of Sodium Laureth-5 Carboxylate
[4]Added 0.23% w/w of a 22% active solution to give 0.05% w/w of Sodium Laureth-5 Carboxylate
[5]Added 0.5% w/w of a 60 parts Caprylic Acid: 40 parts Capric Acid mixture

Example 2—Antimicrobial Testing

The disinfectant formulas from Example 1 were tested for antimicrobial effectiveness by the following method.

Principle of Method: A sample of disinfectant (diluted or full strength) was mixed with a pure strain of a microorganism. The resultant mixture was plated and efficacy was determined by counting viable bacterial colonies.

Microorganisms: All testing used EZ-PEC™ kits containing lyophilized pellets of each microorganism and vials of Hydrating Fluid commercially available from Microbiologics except for *Mycobacterium avium*. Lyophilized pellets of *Mycobacterium avium* were custom made by Microbiologics. Standard strains of *Pseudomonas aeruginosa* (derived from ATCC® 9027), *Escherichia coli* (derived from ATCC® 8739), *Staphylococcus aureus* (derived from ATCC® 6538), *Candida albicans* (derived from ATCC® 10231), *Aspergillus brasiliensis* (derived from ATCC® 16404), and *Mycobacterium avium* (derived from ATCC® 700898) were used.

Microbial Stock Preparation: The Hydrating Fluid was warmed in an incubator at 35° C. for 30 min. After 30 min, 2 pellets of microorganism were added to an amount of the Hydrating Fluid using sterile forceps. The solution was returned to the incubator for 30 min. The solution was gently shaken for complete dissolution.

Procedure: A 40 µL sample of the microbial stock solution was added to 4 mL of full strength or diluted disinfectant. A timer was set to count out a predetermined contact time (e.g. 30 sec. or 1 min.) of the microorganism to the disinfectant. At the end of the predetermined contact time, a 1 mL sample of the disinfectant/bacteria solution was added to 9 mL of DIE neutralizing broth. The D/E broth neutralizes the disinfectant and ends the contact time as soon as the sample is placed in the D/E broth. Then a 50 µL sample of the D/E broth mixture was plated onto an appropriate agar plate and spread evenly over the agar surface. The plates were incubated for a period of time and then the CFUs remaining on the plates were counted. The incubation temperatures and times were as follows: *Pseudomonas aeruiginosa:* 35-37° C. for 24-48 hours; *Escherichia coli:* 35-37° C. for 18-24 hours; *Staphylococcus aureus:* 35-37° C. for 24-48 hours; *Aspergillus brasiliensis:* 24-26° C. for 48-72 hours; *Candida albicans:* 35-37° C. for 24-48 hours; and *Mycobacterium avium:* 35-37° C. for 14 days. The $\log_{10}$ reduction was then calculated. The log reduction was calculated using the formula: $\log_{10}$ reduction=$\log_{10}$ (theoretical organisms plated)−$\log_{10}$ (average plate CFUs). Note: The $\log_{10}$ reduction values are represented as log reductions compared to a quantitative control plate in which no organisms were killed. If a quantitative control was not available for a run, log reductions were calculated via the labeled bacterial concentration of the source culture. A result of 0 average plate CFU's indicate that no CFU's were present indicating a complete kill for a given trial. A result of TNTC indicates that colonies for a given trial were too numerous to count and therefore a log reduction cannot be calculated.

The results of the formulas tested against *Staphylococcus aureus* (derived from ATCC® 6538) are shown in Tables 2, 3, 4 and 4a below.

TABLE 2

Formula A Diluted against *Staph Aureus*. Dilution ratio: 1 part Formula:30 parts DI Water

| Trial | Contact Time | Theoretical CFU's Plated per Plate | Average Plate CFU's | $\log_{10}$ Reduction |
|---|---|---|---|---|
| 1 | 1 min | $2.5 \times 10^3$ | >500 | <0.70 |
| 2 | 1 min | $2.5 \times 10^3$ | >500 | <0.70 |
| 3 | 1 min | $2.5 \times 10^3$ | TNTC | — |
| 4 | 1 min | $2.5 \times 10^3$ | TNTC | — |

TABLE 3

Formula B Diluted against *Staph Aureus*. Dilution ratio: 1 part Formula:30 parts DI Water

| Trial | Contact Time | Theoretical CFU's Plated per Plate | Average Plate CFU's | $\log_{10}$ Reduction |
|---|---|---|---|---|
| 1 | 1 min | $2.5 \times 10^3$ | 0 | ≥3.40 |
| 2 | 1 min | $2.5 \times 10^3$ | 0 | ≥3.40 |

TABLE 4

Formula C Full Strength against *Staph Aureus*

| Trial | Contact Time | Theoretical CFU's Plated per Plate | Average Plate CFU's | $\log_{10}$ Reduction |
|---|---|---|---|---|
| 1 | 1 min | $1.25 \times 10^4$ | 0 | ≥4.10 |
| 2 | 1 min | $2.50 \times 10^4$ | 0 | ≥4.40 |

TABLE 4a

Formula F Full Strength against *Staph Aureus*

| Trial | Contact Time | Theoretical CFU's Plated per Plate | Average Plate CFU's | $\log_{10}$ Reduction |
|---|---|---|---|---|
| 1 | 1 min | $2.25 \times 10^3$ | 0 | ≥3.35 |
| 2 | 1 min | $2.25 \times 10^3$ | 0 | ≥3.35 |
| 3 | 1 min | $2.25 \times 10^3$ | 0 | ≥3.35 |
| 4 | 1 min | $2.25 \times 10^3$ | 0 | ≥3.35 |
| 5 | 1 min | $2.25 \times 10^3$ | 0 | ≥3.35 |
| 6 | 1 min | $2.25 \times 10^3$ | 0 | ≥3.35 |
| 7 | 1 min | $2.25 \times 10^3$ | 0 | ≥3.35 |
| 8 | 1 min | $2.25 \times 10^3$ | 0 | ≥3.35 |
| 9 | 1 min | $2.25 \times 10^3$ | 0 | ≥3.35 |
| 10 | 1 min | $2.25 \times 10^3$ | 0 | ≥3.35 |
| 11 | 1 min | $2.25 \times 10^3$ | 0 | ≥3.35 |
| 12 | 1 min | $2.25 \times 10^3$ | 0 | ≥3.35 |
| 13 | 1 min | $2.25 \times 10^3$ | 0 | ≥3.35 |
| 14 | 1 min | $2.25 \times 10^3$ | 0 | ≥3.35 |
| 15 | 1 min | $2.25 \times 10^3$ | 0 | ≥3.35 |
| 16 | 1 min | $2.25 \times 10^3$ | 0 | ≥3.35 |

The results shown in tables 2 and 3 indicate that the presence of Sodium Laureth-5 Carboxylate in the formula (Formula B) provides an increased antimicrobial effect against Staph *Aureus*. Additionally, Formula B is microbicidal against Staph *Aureus*, even in a diluted strength. Formulas C and F are also microbicidal against Staph *Aureus*.

The results of the formulas tested against *Pseudomonas aeruginosa* (derived from ATCC® 9027) are shown in tables 5 and 6 below.

TABLE 5

Formula A Diluted against *P. Aeruginosa*. Dilution ratio: 1 part Formula:74 parts DI Water

| Trial | Contact Time | Theoretical CFU's Plated per Plate | Average Plate CFU's | $Log_{10}$ Reduction |
|---|---|---|---|---|
| 1 | 1 min | $2.5 \times 10^3$ | 0 | ≥3.40 |
| 2 | 1 min | $2.5 \times 10^3$ | 0 | ≥3.40 |

TABLE 6

Formula F Diluted against *P. Aeruginosa*. Dilution ratio: 1 part Formula:74 parts DI Water

| Trial | Contact Time | Theoretical CFU's Plated per Plate | Average Plate CFU's | $Log_{10}$ Reduction |
|---|---|---|---|---|
| 1 | 1 min | $2.5 \times 10^3$ | 0 | ≥3.40 |
| 2 | 1 min | $2.5 \times 10^3$ | 0 | ≥3.40 |
| 3 | 1 min | $2.5 \times 10^3$ | 0 | ≥3.40 |
| 4 | 1 min | $2.5 \times 10^3$ | 0 | ≥3.40 |
| 5 | 1 min | $2.5 \times 10^3$ | 0 | ≥3.40 |
| 6 | 1 min | $2.5 \times 10^3$ | 0 | ≥3.40 |
| 7 | 1 min | $2.5 \times 10^3$ | 0 | ≥3.40 |
| 8 | 1 min | $2.5 \times 10^3$ | 0 | ≥3.40 |
| 9 | 1 min | $2.5 \times 10^3$ | 0 | ≥3.40 |
| 10 | 1 min | $2.5 \times 10^3$ | 0 | ≥3.40 |

The results shown in tables 5 and 6 indicated that Formula A and Formula F are microbicidal against *Pseudomonas aeruginosa* even in a diluted strength.

The results of the formulas tested against *Escherichia coli* (derived from ATCC® 8739) are shown in tables 7-9 below.

TABLE 7

Formula A Diluted against *E. Coli*. Dilution ratio: 1 part Formula:21.5 parts DI Water

| Trial | Contact Time | Theoretical CFU's Plated per Plate | Average Plate CFU's | $Log_{10}$ Reduction |
|---|---|---|---|---|
| 1 | 1 min | $2.5 \times 10^3$ | >200 | <1.1 |
| 2 | 1 min | $2.5 \times 10^3$ | >200 | <1.1 |

TABLE 8

Formula B Diluted against *E. Coli*. Dilution ratio: 1 part Formula:22.75 parts DI Water

| Trial | Contact Time | Theoretical CFU's Plated per Plate | Average Plate CFU's | $Log_{10}$ Reduction |
|---|---|---|---|---|
| 1 | 1 min | $2.5 \times 10^3$ | 16 | <2.19 |
| 2 | 1 min | $2.5 \times 10^3$ | 26 | <1.98 |

TABLE 9

Formula F Full Strength against *E. Coli*

| Trial | Contact Time | Theoretical CFU's Plated per Plate | Average Plate CFU's | $Log_{10}$ Reduction |
|---|---|---|---|---|
| 1 | 1 min | $2.5 \times 10^3$ | 0 | ≥3.40 |
| 2 | 1 min | $2.5 \times 10^3$ | 0 | ≥3.40 |
| 3 | 1 min | $2.5 \times 10^3$ | 0 | ≥3.40 |
| 4 | 1 min | $2.5 \times 10^3$ | 0 | ≥3.40 |
| 5 | 1 min | $2.5 \times 10^3$ | 0 | ≥3.40 |
| 6 | 1 min | $2.5 \times 10^3$ | 0 | ≥3.40 |
| 7 | 1 min | $2.5 \times 10^3$ | 0 | ≥3.40 |
| 8 | 1 min | $2.5 \times 10^3$ | 0 | ≥3.40 |
| 9 | 1 min | $2.5 \times 10^3$ | 0 | ≥3.40 |
| 10 | 1 min | $2.5 \times 10^3$ | 0 | ≥3.40 |

The results shown in table 9 indicate that Formula F is microbicidal against *E. Coli*.

The results of the formulas tested against *Aspergillus brasiliensis* (derived from ATCC® 16404) are shown in tables 10-18 below.

TABLE 10

Formula B Full Strength against *A. Brasiliensis*

| Trial | Contact Time | Theoretical CFU's Plated per Plate | Average Plate CFU's | $Log_{10}$ Reduction |
|---|---|---|---|---|
| 1 | 1 min | $2.5 \times 10^3$ | TNTC | — |
| 2 | 1 min | $2.5 \times 10^3$ | TNTC | — |

TABLE 11

Formula C Diluted against *A. Brasiliensis*. Dilution ratio: 1 part Formula:4 parts DI Water

| Trial | Contact Time | Theoretical CFU's Plated per Plate | Average Plate CFU's | $Log_{10}$ Reduction |
|---|---|---|---|---|
| 1 | 1 min | $2.5 \times 10^3$ | TNTC | — |
| 2 | 1 min | $2.5 \times 10^3$ | TNTC | — |

TABLE 12

Formula C Full Strength against *A. Brasiliensis*

| Trial | Contact Time | Theoretical CFU's Plated per Plate | Average Plate CFU's | $Log_{10}$ Reduction |
|---|---|---|---|---|
| 1 | 1 min | $2.5 \times 10^3$ | 0 | ≥3.40 |
| 2 | 1 min | $2.5 \times 10^3$ | 0 | ≥3.40 |
| 3 | 1 min | $2.5 \times 10^3$ | 8 | <2.50 |
| 4 | 1 min | $2.5 \times 10^3$ | 10 | <2.40 |

TABLE 13

Formula D Diluted against *A. Brasiliensis*. Dilution ratio: 1 part Formula:3.5 parts DI Water

| Trial | Contact Time | Theoretical CFU's Plated per Plate | Average Plate CFU's | $Log_{10}$ Reduction |
|---|---|---|---|---|
| 1 | 1 min | $2.5 \times 10^3$ | ~200 | <1.10 |
| 2 | 1 min | $2.5 \times 10^3$ | ~200 | <1.10 |

TABLE 14

Formula D Full Strength against *A. Brasiliensis*

| Trial | Contact Time | Theoretical CFU's Plated per Plate | Average Plate CFU's | $Log_{10}$ Reduction |
|---|---|---|---|---|
| 1 | 1 min | $2.5 \times 10^3$ | 0 | ≥3.40 |
| 2 | 1 min | $2.5 \times 10^3$ | 0 | ≥3.40 |

TABLE 15

Formula E Diluted against *A. Brasiliensis*. Dilution ratio: 1 part Formula:3.5 part DI Water

| Trial | Contact Time | Theoretical CFU's Plated per Plate | Average Plate CFU's | $Log_{10}$ Reduction |
|---|---|---|---|---|
| 1 | 1 min | $2.5 \times 10^3$ | 12 | <2.32 |
| 1 | 1 min | $2.5 \times 10^3$ | 15 | <2.22 |
| 1 | 1 min | $2.5 \times 10^3$ | 7 | <2.55 |

TABLE 16

Formula E Full Strength against *A. Brasiliensis*

| Trial | Contact Time | Theoretical CFU's Plated per Plate | Average Plate CFU's | $Log_{10}$ Reduction |
|---|---|---|---|---|
| 1 | 1 min | $2.5 \times 10^3$ | 0 | ≥3.40 |
| 2 | 1 min | $2.5 \times 10^3$ | 0 | ≥3.40 |

TABLE 17

Formula F Diluted against *A. Brasiliensis*. Dilution ration: 1 part Formula:4 parts DI Water

| Trial | Contact Time | Theoretical CFU's Plated per Plate | Average Plate CFU's | $Log_{10}$ Reduction |
|---|---|---|---|---|
| 1 | 1 min | $2.5 \times 10^3$ | 0 | ≥3.40 |
| 2 | 1 min | $2.5 \times 10^3$ | 1 | ≤3.40 |
| 3 | 1 min | $2.5 \times 10^3$ | 19 | <2.12 |
| 4 | 1 min | $2.5 \times 10^3$ | 6 | <2.62 |

TABLE 18

Formula F Full Strength against *A. Brasiliensis*

| Trial | Contact Time | Theoretical CFU's Plated per Plate | Average Plate CFU's | $Log_{10}$ Reduction |
|---|---|---|---|---|
| 1 | 1 min | $2.5 \times 10^3$ | 0 | ≥3.40 |
| 2 | 1 min | $2.5 \times 10^3$ | 0 | ≥3.40 |
| 3 | 30 sec | $2.5 \times 10^3$ | 0 | ≥3.40 |
| 4 | 30 sec | $2.5 \times 10^3$ | 0 | ≥3.40 |

The results shown in tables 10-18 indicate that full strength Formulas D, E, and F are microbicidal against *A. Brasiliensis*.

The results of the formula tested against *Candida albicans* (derived from ATCC® 10231) are shown in Table 19 below.

TABLE 19

Formula F Full Strength against *C. Albicans*

| Trial | Contact Time | Theoretical CFU's Plated per Plate | Average Plate CFU's | $Log_{10}$ Reduction |
|---|---|---|---|---|
| 1 | 30 sec | $2.5 \times 10^4$ | 0 | ≥4.40 |
| 2 | 30 sec | $2.5 \times 10^3$ | 0 | ≥3.40 |

The results shown in table 19 indicate that Formula F is fungicidal against *C. Albicans*.

The results of the formula tested against *Mycobacterium avium* (derived from ATCC® 700898) are shown in Table 20 below.

TABLE 20

Formula F Full Strength against *Mycobacterium Avium*

| Trial | Contact Time | Theoretical CFU's Plated per Plate | Average Plate CFU's | $Log_{10}$ Reduction |
|---|---|---|---|---|
| 1 | 1 min | $5.05 \times 10^3$ | 0 | ≥3.70 |
| 2 | 1 min | $5.05 \times 10^3$ | 0 | ≥3.70 |

The results shown in table 20 indicates that Formula F is mycobactericidal against *Mycobacterium avium*.

As can be seen in the results tables, the full-strength Formula F exhibited microbicidal activity against *Escherichia coli* (gram negative bacteria), *Staphylococcus aureus* (gram positive bacteria), *Aspergillus brasiliensis* (mold), and *Mycobacterium avium* (mycobacteria). Formula F also exhibited fungicidal activity against *Candida albicans* (yeast). Full strength Formula C exhibited microbicidal activity against *Staphylococcus aureus* (gram positive bacteria) and diluted Formula C exhibited microbicidal activity against *Pseudomonas aeruginosa* (gram negative bacteria).

Example 3—Additional Testing for Antimicrobial/Microbicidal Activity Against Mycobacteria The disinfectant formulas in Table 1 above and Tables 21 and 22 below were tested for antimicrobial and microbicidal efficacy and synergism against *Mycobacterium avium* (derived from ATCC® 700898). All disinfectant formulas were tested at full strength, i.e. no formula dilution.

TABLE 21

| Ingredient | CAS No. | G | H | I | J | K | L | M | N |
|---|---|---|---|---|---|---|---|---|---|
| Hydrogen Peroxide[1] | 7722-84-1 | 0.5 | 0.5 | 0.5 | 0.5 | 0.5 | 0.0 | 0.5 | 0.5 |
| Etidronic Acid (HEDP)[2] | 2809-21-4 | 0.3 | 0.3 | 0.3 | 0.3 | 0.3 | 0.3 | 0.3 | 0.3 |
| Formic Acid | 64-18-6 | — | — | — | — | — | — | — | — |
| Sodium Laureth-5 Carboxylate[3] | 33939-64-9 | — | 0.05 | — | — | — | — | — | — |
| Sodium Lauryl Sulfate | 151-21-3 | — | — | 0.4 | — | — | — | — | — |
| Caprylic Acid | 124-07-2 | — | — | — | 0.3[4] | — | 0.3[4] | 0.5 | — |
| Capric Acid | 334-48-5 | — | — | — | 0.2[4] | — | 0.2[4] | — | 0.5 |

Formula ID & % w/w of tota composition

TABLE 21-continued

| | | Formula ID & % w/w of tota composition | | | | | | | |
|---|---|---|---|---|---|---|---|---|---|
| Ingredient | CAS No. | G | H | I | J | K | L | M | N |
| Salicylic Acid | 69-72-7 | — | — | — | — | 0.18 | — | — | — |
| DI Water | — | q.s. to 100% | q.s. to 100% | q.s. to 100% | q.s. to 100% | q.s. to 100% | q.s. to 100% | q.s. to 100% | q.s. to 100% |
| pH readings | | 1.96 | 1.88 | 1.99 | 1.87 | 1.86 | 1.93 | 3.65 | 3.48 |

[1] added 1.43% w/w of a 35% active solution to give 0.5% w/w of Hydrogen Peroxide
[2] added 0.5% w/w of a 60% active solution to give 0.3% w/w of Etidronic Acid (HEDP)
[3] added 0.23% w/w of a 22% active solution to give 0.05% w/w of Sodium Laureth-5 Carboxylate
[4] added 0.5% w/w of a 60 parts Caprylic Acid: 40 parts Capric Acid mixture

TABLE 22

| | | Formula ID & % w/w of total composition | | | |
|---|---|---|---|---|---|
| Ingredient | CAS No. | O | P | Q | R |
| Hydrogen Peroxide[1] | 7722-84-1 | 0.5 | 0.5 | 0.5 | 0.5 |
| Etidronic Acid (HEDP)[2] | 2809-21-4 | 0.3 | 0.3 | 0.3 | 0.3 |
| Formic Acid | 64-18-6 | 0.5 | 0.5 | 0.5 | 0.5 |
| Sodium Laureth-5 Carboxylate[3] | 33939-64-9 | 0.05 | 0.05 | 0.05 | 0.05 |
| Sodium Lauryl Sulfate | 151-21-3 | 0.4 | 0.4 | 0.4 | 0.4 |
| Caprylic Acid | 124-07-2 | — | 0.2 | — | 0.2 |
| Capric Acid | 334-48-5 | — | — | — | — |
| Salicylic Acid | 69-72-7 | — | — | 0.18 | 0.18 |
| DI Water | — | q.s. to 100% | q.s. to 100% | q.s. to 100% | q.s. to 100% |
| pH readings | | 1.93 | 1.92 | 1.91 | 1.88 |

[1] added 1.43% w/w of a 35% active solution to give 0.5% w/w of Hydrogen Peroxide
[2] added 0.5% w/w of a 60% active solution to give 0.3% w/w of Etidronic Acid (HEDP)
[3] added 0.23% w/w of a 22% active solution to give 0.05% w/w of Sodium Laureth-5 Carboxylate The disinfectant formulas in Table 1, Table 21 and Table 22 were tested for antimicrobial and microbicidal synergism by the following method.

Principle of Method: A sample of disinfectant (full strength) was mixed with a pure strain of the microorganism. The resultant mixture was plated and efficacy was determined by counting viable bacterial colonies.

Microorganisms: All testing used lyophilized pellets of *Mycobacterium avium* (derived from ATCC® 700898) custom made by Microbiologics and Hydrating Fluid made by Microbiologics.

Microbial Stock Preparation: The Hydrating Fluid was warmed in an incubator at 35° C. for 30 min. After 30 min, pellets of microorganism were added to an amount of the Hydrating Fluid using sterile forceps. The solution was returned to the incubator for 30 min. The solution was gently shaken for complete dissolution.

Procedure: A 40 µL sample of the microbial stock solution was added to 4 mL of full-strength disinfectant. A timer was set to count out a predetermined contact time (e.g. 30 sec. or 1 min.) of the microorganism to the disinfectant. At the end of the predetermined contact time, a 1 mL sample of the disinfectant/bacteria solution was added to 9 mL of D/E neutralizing broth. The D/E broth neutralizes the disinfectant and ends the contact time as soon as the sample is placed in the D/E broth. Then a 50 µL sample of the D/E broth mixture was plated onto an appropriate agar plate and spread evenly over the agar surface. The plates were incubated at 35-37° C. for 14 days and then the CFUs remaining on the plates were counted. The $\log_{10}$ reduction was then calculated. The log reduction was calculated using the formula:

$\log_{10}$ reduction=$\log_{10}$ (theoretical organisms plated)–$\log_{10}$ (average plate CFUs). Note: The $\log_{10}$ reduction values are represented as log reductions compared to a quantitative control plate in which no organisms were killed. If a quantitative control was not available for a run, log reductions were calculated via the labeled bacterial concentration of the source culture. A result of 0 average plate CFU's indicate that no CFU's were present indicating a complete kill for a given trial. A result of TNTC indicates that colonies for a given trial were too numerous to count and therefore a log reduction cannot be calculated.

Results of the mycobacteria studies are shown in Table 23 below.

TABLE 23

| Formula | Trial | Contact Time | Theoretical CFU's Plated per Plate | Average Plate CFU's | $\log_{10}$ Reduction |
|---|---|---|---|---|---|
| A | 1 | 1 min | $8.586 \times 10^3$ | TNTC | — |
| A | 2 | 1 min | $1.56 \times 10^4$ | TNTC | — |
| B | 1 | 1 min | $8.586 \times 10^3$ | TNTC | — |
| B | 2 | 1 min | $1.56 \times 10^4$ | TNTC | — |
| C | 1 | 1 min | $8.586 \times 10^3$ | TNTC | — |
| C | 2 | 1 min | $1.56 \times 10^4$ | TNTC | — |
| D | 1 | 1 min | $8.586 \times 10^3$ | 0 | ≥3.93 |
| D | 2 | 1 min | $1.56 \times 10^4$ | 0 | ≥4.19 |
| E | 1 | 1 min | $8.586 \times 10^3$ | TNTC | — |
| E | 2 | 1 min | $1.56 \times 10^4$ | TNTC | — |
| F | 1 | 1 min | $8.586 \times 10^3$ | 0 | ≥3.93 |
| F | 2 | 1 min | $1.56 \times 10^4$ | 0 | ≥4.19 |
| G | 1 | 1 min | $8.586 \times 10^3$ | TNTC | — |
| G | 2 | 1 min | $1.56 \times 10^4$ | TNTC | — |
| H | 1 | 1 min | $8.586 \times 10^3$ | TNTC | — |
| H | 2 | 1 min | $1.56 \times 10^4$ | TNTC | — |
| I | 1 | 1 min | $8.586 \times 10^3$ | TNTC | — |
| I | 2 | 1 min | $1.56 \times 10^4$ | TNTC | — |
| J | 1 | 1 min | $8.586 \times 10^3$ | 0 | ≥3.93 |
| J | 2 | 1 min | $1.56 \times 10^4$ | 0 | ≥4.19 |
| K | 1 | 1 min | $8.586 \times 10^3$ | TNTC | — |
| K | 2 | 1 min | $1.56 \times 10^4$ | TNTC | — |
| L | 1 | 1 min | $8.3 \times 10^3$ | 0 | ≥3.92 |
| M | 1 | 1 min | $8.3 \times 10^3$ | 0 | ≥3.92 |
| N | 1 | 1 min | $8.3 \times 10^3$ | 369 | 1.35 |
| O | 1 | 1 min | $1.1 \times 10^4$ | 2100 | 0.72 |
| O | 2 | 1 min | $1.1 \times 10^4$ | 2260 | 0.69 |
| P | 1 | 1 min | $1.1 \times 10^4$ | 110 | 2.00 |
| P | 2 | 1 min | $1.1 \times 10^4$ | 140 | 1.90 |
| Q | 1 | 1 min | $1.1 \times 10^4$ | 120 | 1.96 |
| Q | 2 | 1 min | $1.1 \times 10^4$ | 150 | 1.87 |
| R | 1 | 1 min | $1.3 \times 10^6$ | 0 | ≥6.11 |
| R | 2 | 1 min | $1.3 \times 10^6$ | 0 | ≥6.11 |

As seen in Table 23, the mycobacteria study results for formulas O, P, Q, and R demonstrate a synergistic antimicrobial effect against mycobacteria between caprylic acid and salicylic acid when both are present in the formula (Formula R) at concentrations of 0.2% w/w and 0.18% w/w respectively with a contact time of 1 minute. Additionally, Formula R is mycobactericidal and demonstrates a greater than 6 log reduction of mycobacteria.

Example 4—Hydrogen Peroxide Disinfectant Formulas Containing Sodium Olefin Sulfonate Surfactants The disinfectant formula (Formula S) listed in Table 24 was made according to the following procedure: The Etidronic Acid (HEDP) was added to the water and mixed until dissolved. Next, the hydrogen peroxide was added and mixed until dissolved. Then, the remaining ingredients were added in no particular order and mixed until dissolved. The formulas were translucent liquids. The formula listed in Table 1 is a full-strength formula ready for use.

TABLE 24

Formula S

| Ingredient | CAS No. | % w/w of total composition |
|---|---|---|
| Hydrogen Peroxide[1] | 7722-84-1 | 0.5 |
| Etidronic Acid (HEDP)[2] | 2809-21-4 | 0.3 |
| Formic Acid | 64-18-6 | 0.5 |
| Sodium (C14-C16) Olefin Sulfonate[3] | 68439-57-6 | 0.4 |
| Caprylic Acid | 124-07-2 | 0.5 |
| Salicylic Acid | 69-72-7 | 0.18 |
| DI Water | | q.s. to 100% | pH reading: 1.7
[1] added 1.43% w/w of a 35% active solution to give 0.5% w/w of Hydrogen Peroxide
[2] added 0.5% w/w of a 60% active solution to give 0.3% w/w of Etidronic Acid (HEDP)
[3] added 1.03% w/w of a 39% active solution to give 0.4% w/w of sodium (C14-C16) olefin sulfonate The formula in Table 24 (Formula S) was tested for antimicrobial effectiveness by the method described in Example 2 above and the results are shown in Tables 25-30 below. All the disinfectant solutions were at full strength.

TABLE 25

Formula S Full Strength against *Candida Albicans*

| Trial | Contact Time | Theoretical CFUs per plate | Average Plate CFUs | $Log_{10}$ Reduction |
|---|---|---|---|---|
| 1 | 1 min | 1375 | 0 | ≥3.14 |
| 2 | 1 min | 1375 | 0 | ≥3.14 |

TABLE 26

Formula S Full Strength against *Pseudomonas Aeruginosa*

| Trial | Contact Time | Theoretical CFUs per plate | Average Plate CFUs | $Log_{10}$ Reduction |
|---|---|---|---|---|
| 1 | 1 min | 900 | 0 | ≥2.95 |

TABLE 27

Formula S Full Strength against *Mycobacterium Avium*

| Trial | Contact Time | Theoretical CFUs per plate | Average Plate CFUs | $Log_{10}$ Reduction |
|---|---|---|---|---|
| 1 | 1 min | 8500 | 0 | ≥3.93 |
| 2 | 1 min | 8500 | 0 | ≥3.93 |

TABLE 27-continued

Formula S Full Strength against *Mycobacterium Avium*

| Trial | Contact Time | Theoretical CFUs per plate | Average Plate CFUs | $Log_{10}$ Reduction |
|---|---|---|---|---|
| 3 | 1 min | 34000 | 0 | ≥4.53 |
| 4 | 1 min | 34000 | 0 | ≥4.53 |

TABLE 28

Formula S Full Strength against *Staph Aureus*

| Trial | Contact Time | Theoretical CFUs per plate | Average Plate CFUs | $Log_{10}$ Reduction |
|---|---|---|---|---|
| 1 | 1 min | 1225 | 0 | ≥3.09 |
| 2 | 1 min | 1225 | 0 | ≥3.09 |
| 3 | 1 min | 1225 | 0 | ≥3.09 |
| 4 | 1 min | 245000 | 0 | ≥5.39 |

TABLE 29

Formula S Full Strength against *Aspergillus Brasiliensis*

| Trial | Contact Time | Theoretical CFUs per plate | Average Plate CFUs | $Log_{10}$ Reduction |
|---|---|---|---|---|
| 1 | 1 min | 1525 | 0 | ≥3.18 |
| 2 | 1 min | 1525 | 0 | ≥3.18 |
| 3 | 1 min | 305000 | 1 | 5.48 |

TABLE 30

Formula S Full Strength against *E. Coli*

| Trial | Contact Time | Theoretical CFUs per plate | Average Plate CFUs | $Log_{10}$ Reduction |
|---|---|---|---|---|
| 1 | 1 min | 1700 | 0 | ≥3.23 |
| 2 | 1 min | 1700 | 0 | ≥3.23 |
| 3 | 1 min | 340000 | 0 | ≥5.53 |

The formula in Table 24 (Formula S) was tested for antimicrobial effectiveness by the method described in Example 2 above except that the amount of the bacterial stock solution was 0.1 mL and the amount of disinfectant was 1 mL and the results are shown in Tables 31-33 below. All the disinfectant solutions were at full strength. In Table 33, the commercial product OPTIM® 1 (active ingredient 0.5% hydrogen peroxide) available from SciCan and manufactured by VIROX Technologies, Inc. was the disinfectant solution (full strength) tested against *Mycobacterium avium*.

TABLE 31

Formula S Full Strength against *E. Coli*

| Trial | Contact Time | Theoretical CFUs per plate | Average Plate CFUs | $Log_{10}$ Reduction |
|---|---|---|---|---|
| 1 | 1 min | 1700 | 0 | ≥3.23 |
| 2 | 1 min | 1700 | 0 | ≥3.23 |
| 3 | 1 min | 34000 | 0 | ≥4.53 |

TABLE 32

Formula S Full Strength against *Mycobacterium Avium*

| Trial | Contact Time | Theoretical CFUs per plate | Average Plate CFUs | $Log_{10}$ Reduction |
|---|---|---|---|---|
| 1 | 1 min | 8500 | 0 | ≥3.93 |
| 2 | 1 min | 8500 | 0 | ≥3.93 |
| 3 | 1 min | 850000 | 0 | ≥5.93 |
| 4 | 1 min | 850000 | 0 | ≥5.93 |

TABLE 33

Optim® 1 Full Strength against *Mycobacterium Avium*

| Trial | Contact Time | Theoretical CFUs per plate | Average Plate CFUs | $Log_{10}$ Reduction |
|---|---|---|---|---|
| 1 | 1 min | 850000 | 10 | 4.93 |
| 2 | 1 min | 850000 | 50 | 3.23 |

The results shown in Tables 25-32 show that Formula S exhibited bactericidal activity against *Pseudomonas aeruginosa* and *Escherichia coli* (gram negative bacteria), and *Staphylococcus aureus* (gram positive bacteria). Formula S exhibited mycobactericidal activity against *Mycobacterium avium* (mycobacteria). Formula S exhibited fungicidal activity against *Candida albicans* (yeast). Formula S exhibited antimicrobial activity or microbicidal activity against *Aspergillus brasiliensis* (mold).

As seen in Table 33, Optim® 1 was not mycobactericidal against *Mycobacterium avium* (mycobacteria) whereas Formula S was mycobactericidal against *Mycobacterium avium* (mycobacteria) as seen in Table 32. Additionally, Formula S had a greater log 10 reduction than Optim® 1. These results are surprising because Formula S which does not contain a volatile C1-C7 alcohol performed better against mycobacteria than Optim® 1 which does contain a volatile C1-C7 alcohol (benzyl alcohol).

Example 5—Antimicrobial/Microbicidal Synergism Testing for Hydrogen Peroxide Disinfectant Formulas Containing Sodium Olefin Sulfonate Surfactants The disinfectant formulas listed in Table 34 will be tested for made and tested for antimicrobial and microbiocidal synergism.

TABLE 34

| | | Formula ID & % w/w of total composition | | | |
|---|---|---|---|---|---|
| Ingredient | CAS No. | T | U | V | W |
| Hydrogen Peroxide[1] | 7722-84-1 | 0.5 | 0.5 | 0.5 | 0.5 |
| Etidronic Acid (HEDP)[2] | 2809-21-4 | 0.3 | 0.3 | 0.3 | 0.3 |
| Formic Acid | 64-18-6 | 0.5 | 0.5 | 0.5 | 0.5 |
| Sodium C14-C16 Olefin Sulfonate[3] | 68439-57-6 | 0.4 | 0.4 | 0.4 | 0.4 |
| Caprylic Acid | 124-07-2 | — | 0.2 | — | 0.2 |
| Salicylic Acid | 69-72-7 | — | — | 0.18 | 0.18 |
| DI Water | — | q.s. to 100% | q.s. to 100% | q.s. to 100% | q.s. to 100% |

[1]will add 1.43% w/w of a 35% active solution to give 0.5% w/w of Hydrogen Peroxide
[2]will add 0.5% w/w of a 60% active solution to give 0.3% w/w of Etidronic Acid (HEDP)
[3]will add 1.03% w/w of a 39% active solution to give 0.4% w/w of sodium (C14-C16) olefin sulfonate The disinfectant formulas from Table 34 will be tested for antimicrobial and microbicidal synergism by the following method.

Principle of Method: A sample of disinfectant (full strength) will be mixed with a pure strain of a microorganism. The resultant mixture will be plated and efficacy will be determined by counting viable bacterial colonies.

Microorganisms: All testing will use lyophilized pellets of *Mycobacterium avium* (derived from ATCC® 700898) custom made by Microbiologics and Hydrating Fluid made by Microbiologics.

Microbial Stock Preparation: The Hydrating Fluid will be warmed in an incubator at 35° C. for 30 min. After 30 min, pellets of microorganism will be added to an amount of the Hydrating Fluid using sterile forceps. The solution will be returned to the incubator for 30 min. The solution will be gently shaken for complete dissolution.

Procedure: A 40 μL sample of the microbial stock solution will be added to 4 mL of full strength disinfectant. Alternatively, a 0.1 mL sample of the microbial stock solution will be added to 1 mL of full strength disinfectant. A timer will be set to count out a predetermined contact time (e.g. 30 sec. or 1 min.) of the microorganism to the disinfectant. At the end of the predetermined contact time, a 1 mL sample of the disinfectant/bacteria solution will be added to 9 mL of D/E neutralizing broth. The D/E broth neutralizes the disinfectant and ends the contact time as soon as the sample is placed in the D/E broth. Then a 50 μL sample of the D/E broth mixture will be plated onto an appropriate agar plate and spread evenly over the agar surface. The plates will be incubated for a period of time and then the CFUs remaining on the plates will be counted. The $log_{10}$ reduction will be then calculated.

It is expected that the results of the formulas tested will demonstrate a synergistic antimicrobial effect against mycobacteria between caprylic acid and salicylic acid when both are present in a formula containing sodium C14-C16 olefin sulfonate (Formula W) at concentrations of 0.2% w/w caprylic acid and 0.18% w/w salicylic acid.

The invention claimed is:
1. An aqueous-based disinfecting composition comprising:
(a) hydrogen peroxide at a concentration of 0.1 to 0.9% w/w;
(b) caprylic acid, or a salt thereof, at a concentration of 0.1 to 1% w/w;
(c) salicylic acid, or a salt thereof at a concentration of 0.1 to 1% w/w; and
(d) water,
wherein the composition does not include or is substantially free of a volatile C1-C7 alcohol, wherein the pH of the composition is from about 0.1 to 2, and wherein the composition is capable of exhibiting mycobacteri- cidal activity against mycobacteria on a surface when the composition is in contact with the mycobacteria for at least 1 minute.

2. The composition of claim 1, wherein the surface is a non-porous hard surface.

3. The composition of claim 1, wherein the composition further comprises a sequestering or chelating agent.

4. The composition of claim 3, wherein the sequestering or chelating agent is etidronic acid (HEDP), or a salt thereof, and is at a concentration of about 0.01 to about 5% w/w.

5. The composition of claim 1, wherein the composition further comprises one or more linear monocarboxylic acids with a carbon chain length of C1 to C4, or a salt thereof.

6. The composition of claim 5, wherein the one or more linear monocarboxylic acids with a carbon chain length of C1 to C4, or a salt thereof, is formic acid, or a salt thereof, at a concentration of about 0.01 to about 5% w/w.

7. The composition of claim 1, wherein the composition further comprises one or more surfactants selected from sodium olefin sulfonate surfactants, sodium C8 to C16 alkyl sulfate surfactants, or C12 to C16 linear alkyl ether carboxylic acids, or salts thereof.

8. The composition of claim 7, wherein the sodium olefin sulfonate surfactant is sodium C14-C16 olefin sulfonate at a concentration of about 0.01 to about 5% w/w.

9. The composition of claim 7, wherein the C8 to C16 alkyl sulfate surfactant is sodium lauryl sulfate at a concentration of about 0.01 to about 5% w/w.

10. The composition of claim 7, wherein the C12 to C16 linear alkyl ether carboxylic acids, or salts thereof, is laureth-5 carboxylic acid, or a salt thereof, at a concentration of about 0.01 to about 5% w/w.

11. The composition of claim 1, wherein the composition further comprises a fragrance or a dye.

12. The composition of claim 1, wherein the hydrogen peroxide is at a concentration of 0.3 to 0.7% w/w.

13. A method of disinfecting or sterilizing a non-porous hard surface, the method comprising:
contacting the non-porous hard surface with the composition of claim 1; and
allowing the composition to remain in contact with the non-porous hard surface for at least 1 minute, thereby disinfecting or sterilizing the non-porous hard surface.

14. A method of disinfecting or sterilizing a non-porous hard surface, the method comprising:
(1) contacting the non-porous hard surface with a composition comprising:
(a) hydrogen peroxide at a concentration of 0.1 to 0.9% w/w;
(b) one or more linear monocarboxylic acids with a carbon chain length of C5 to C12, or a salt thereof, at a concentration of about 0.01 to about 5% w/w;
(c) salicylic acid at a concentration of about 0.01 to about 5% w/w; and
(d) water; and
(2) allowing the composition to remain in contact with the non-porous hard surface for at least 1 minute, thereby disinfecting or sterilizing the non-porous hard surface, wherein the composition does not contain or is substantially free of a volatile C1-C7 alcohol,
wherein the one or more linear monocarboxylic acids with a carbon chain length of C5 to C12, or a salt thereof, is caprylic acid (C8), or a salt thereof, and/or capric acid (C10), or a salt thereof, and wherein the pH of the composition is from about 0.1 to 2.

15. The method of claim 14, wherein the composition further comprises a sequestering or chelating agent.

16. The method of claim 15, wherein the sequestering or chelating agent is etidronic acid (HEDP), or a salt thereof, and is at a concentration of about 0.01 to about 5% w/w.

17. The method of claim 14, wherein the composition further comprises one or more linear monocarboxylic acids with a carbon chain length of C1 to C4, or a salt thereof.

18. The method of claim 17, wherein the one or more linear monocarboxylic acids with a carbon chain length of C1 to C4, or the salt thereof, is formic acid, or a salt thereof, at a concentration of about 0.01 to about 5% w/w.

19. The method of claim 14, wherein the composition further comprises one or more surfactants selected from sodium olefin sulfonate surfactants, sodium C8 to C16 alkyl sulfate surfactants, or C12 to C16 linear alkyl ether carboxylic acids, or salts thereof.

20. The method of claim 14, wherein the non-porous hard surface is at least a portion of the surface of a counter, a furniture, a wall, a floor, a medical equipment, a device, a tool, an instrument, a food preparation or handling equipment, an appliance, a utensil, or a bathroom fixture.

21. The method of claim 14, wherein the non-porous hard surface is not skin or a biological surface.

* * * * *